US011357836B2

(12) United States Patent
Verhoef et al.

(10) Patent No.: US 11,357,836 B2
(45) Date of Patent: *Jun. 14, 2022

(54) PROHEMOSTATIC PROTEINS FOR THE TREATMENT OF BLEEDING

(71) Applicant: Academisch Ziekenhuis Leiden, Leiden (NL)

(72) Inventors: Daniël Verhoef, Leiden (NL); Pieter H. Reitsma, Leiden (NL); Mettine H. A. Bos, Leiden (NL)

(73) Assignee: Academisch Ziekenhuis Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,866

(22) Filed: Dec. 18, 2019

(65) Prior Publication Data

US 2020/0138916 A1 May 7, 2020

Related U.S. Application Data

(63) Continuation of application No. 15/313,881, filed as application No. PCT/NL2015/050377 on May 26, 2015, now Pat. No. 10,537,618.

(30) Foreign Application Priority Data

May 26, 2014 (EP) ..................................... 14169895

(51) Int. Cl.
*A61K 38/48* (2006.01)
*C12N 9/64* (2006.01)
*C07K 14/46* (2006.01)

(52) U.S. Cl.
CPC .......... *A61K 38/4846* (2013.01); *C07K 14/46* (2013.01); *C12N 9/6432* (2013.01); *C12Y 304/21006* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,460,950 A | 10/1995 | Barr et al. | |
| 5,817,309 A | 10/1998 | Nowak et al. | |
| 6,060,300 A | 5/2000 | Raditsch et al. | |
| 6,086,871 A | 7/2000 | Fischer et al. | |
| 6,200,955 B1 | 3/2001 | Harris et al. | |
| 6,624,141 B1 | 9/2003 | Yang et al. | |
| 6,797,492 B2 | 9/2004 | Daugherty et al. | |
| 10,537,618 B2* | 1/2020 | Verhoef ................... | A61P 7/04 |
| 2009/0053185 A1 | 2/2009 | Schulte et al. | |
| 2009/0098119 A1 | 4/2009 | Lu et al. | |
| 2009/0175828 A1 | 7/2009 | Schulte et al. | |
| 2011/0015128 A1 | 1/2011 | Sinha et al. | |
| 2015/0307817 A1 | 10/2015 | Peitersen et al. | |
| 2015/0343034 A1 | 12/2015 | Pittman et al. | |
| 2020/0138917 A1* | 5/2020 | Verhoef ................... | A61P 7/04 |

FOREIGN PATENT DOCUMENTS

| | | |
|---|---|---|
| CN | 101356192 A | 1/2009 |
| CN | 101743309 A | 6/2010 |
| CN | 101802188 A | 8/2010 |
| CN | 102083971 A | 6/2011 |
| EP | 0150126 B1 | 10/1991 |
| EP | 0519596 B1 | 2/2005 |
| JP | 2010-539945 A | 12/2010 |
| JP | 2012-533552 A | 12/2012 |
| JP | 2016-511755 A | 4/2016 |
| JP | 2017-515659 | 6/2017 |
| WO | 2009/042962 A2 | 4/2009 |
| WO | 2014/018120 | 1/2014 |
| WO | 2015/183085 A1 | 12/2015 |

OTHER PUBLICATIONS

Reza et al. "Molecular evolution caught in action: gene duplication and evolution of molecular isoforms of prothrombin activators in *Pseudonaja textilis* (brown snake)" J. Thrombosis and Hemostasis 4:1346-1353. (Year: 2006).*
Krishnaswamy et al., "Contribution of the Prothrombin Fragment 2 Domain to the Function of Factor Va in the Prothrombinase Complex†" Biochemistry 1997, 36, 11, 3319-3330.
Uprichard et al., "Factor X deficiency" Blood Reviews 2002, 16:97-110.
Wienken et al., "Protein-binding assays in biological liquids using microscale thermophoresis" Nature Communications 2010, 1:100.
European Search Report and Search Opinion Received for EP Application No. 20177786, dated Sep. 25, 2020, 8 pages.
Adriaansen, et al., "Samenvatting Medische Jaarverslagen van de Federatie van Nederlandse Trombosediensten," 2011; 1-44).
Andersson et al., "Cloning, Structure, and Expression of the Mitochondrial Cytochrome P-450 Sterol 26-Hydroxylase, a Bile Acid Biosynthetic Enzyme" (1989) J. Biol. Chem. 264, 8222-8229).
Bode et al., "The refined 1.9 A crystal structure of human alpha-thrombin: interaction with D-Phe-Pro-Arg chloromethylketone and significance of the Tyr-Pro-Pro-Trp insertion segment"; EMBO Journal 1989, 8:3467-3475.
Bos et al., "Procoagulanl Adaptation of a Blood Coagulation Prolhrombinase-like Enzyme Complex in Australian Elapid Venom" Toxins vol. 2. No. 6, Jun. 18, 2010 (Jun. 18, 2010). pp. 1554-1567, XP055216133, ISSN: 2072-6651. DOI: 10.339/loxins2061554 p. 1556, paragraph 4, figure 1.
Bos et al., "Venom factor V from the common brown snake escapes hemostatic regulation through procoagulant adaptations", Blood, 2009, 114: 686-692.

(Continued)

*Primary Examiner* — Sudhakar Katakam
*Assistant Examiner* — Zachary J Miknis
(74) *Attorney, Agent, or Firm* — TraskBritt

(57) ABSTRACT

This disclosure relates to recombinant FXa polypeptides that can be used as antidotes to completely or partially reverse an anti-coagulant effect of a coagulation inhibitor in a subject, preferably a direct factor Xa inhibitor. Disclosed herein are recombinant factor Xa proteins and a method of completely or partially reversing an anti-coagulant effect of a coagulation inhibitor in a subject.

4 Claims, 17 Drawing Sheets

Figure 1:
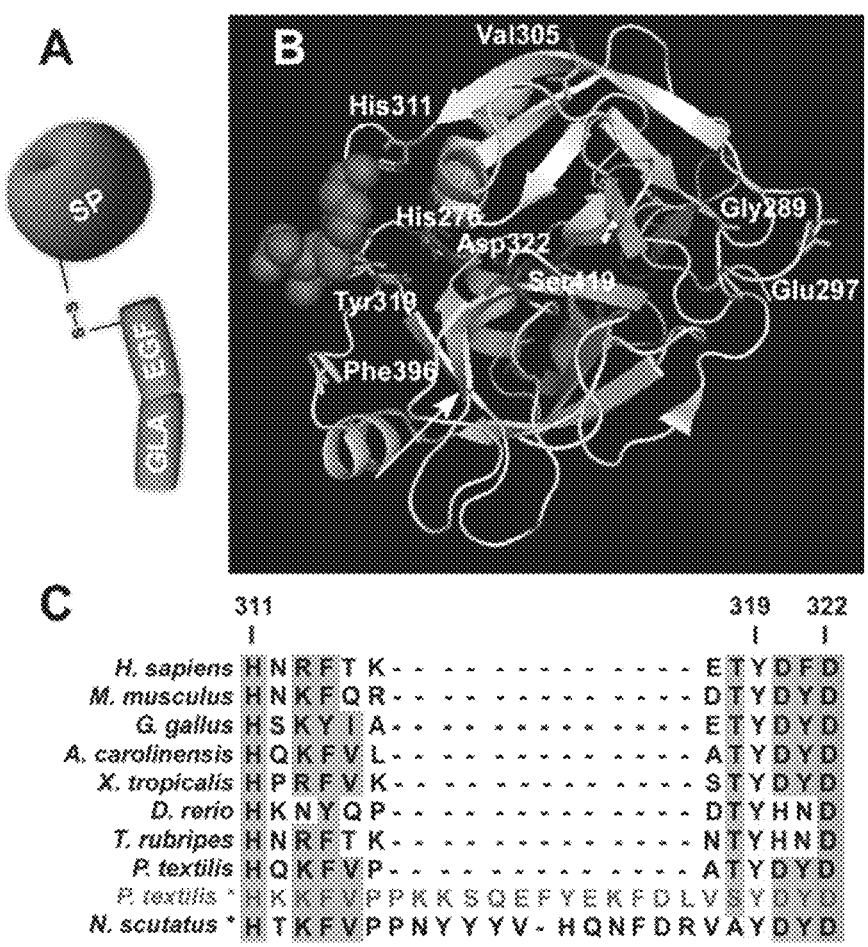

Specification includes a Sequence Listing.

(56) References Cited

OTHER PUBLICATIONS

Bos M and Camire R "Procoagulant Adaptation of a Blood Coagulation Prothombinase-like Enzyme Complex in Australian Elapid Venom" Toxins 2:1554-1567. (Year: 2010).
Bos MH, Camire RM., and Procoagulant adaptation of a blood coagulation prothrombinase-like enzyme complex in australian elapid venom. and Toxins (Basel). Jun. 18, 2010-day [ two ] (6):, 1554-1567.
Camire et al. "Enhanced ?-Carboxylation of Recombinant Factor X Using a Chimeric Construct Containing the Prothrombin Propeptide" Biochemistry 2000, 39, 46, 14322-14329.
Camire, "Prothrombinase Assembly and S1 Site Occupation Restore the Catalytic Activity of FXa Impaired by Mutation at the Sodium-binding Site," J. Biol. Chem. vol. 277, No. 40, Issue of Oct. 4, pp. 37863-37870, 2002.
Chinese Search Report for Chinese Application No. 201580039023, dated Oct. 24, 2019, 2 pages.
Chu et al., "SV40 DNA transfection of cells in suspension: analysis of efficiency of transcription and translation of T-antigen," Gene 1981, 13:197.
Davis et al., Basic Methods in Molecular Biology 1986, Elsevier.
European Communication pursuant to Article 94(3) EPC for European Application No. 15731411, dated Feb. 6, 2019, 4 pages.
European Communication pursuant to Article 94(3) EPC for European Application No. 15731411, dated Nov. 24, 2017, 4 pages.
Frumkin, "Rapid Reversal of Warfarin-Associated Hemorrhage in the Emergency Department by Prothrombin Complex Concentrates," Ann. Emerg Med. 2013, 62:616-626.
Graham et al., "A new technique for the assay of infectivity of human adenovirus 5 DNA," Virology vol. 52, Issue 2, Apr. 1973, pp. 456-467.
Green et al., "Molecular Cloning: A Laboratory Manua," CSHL Press, 2012.
Hemker et al., "Calibrated Automated Thrombin Generation Measurement in Clotting Plasma," Pathophysiol Haemost Thromb 2003; 33:4-15.
Higgins et al., "The Interaction of Bovine Factor V and Factor V-derived Peptides with Phospholipid Vesicles," J. Biol. Chem. vol. 258, No. 10, Issue of May 25, pp. 6503-6508, 1983.
International Search Report for International Application No. PCT/NL15/050377, dated Oct. 7, 2015, 4 pages.
International Written Opinion for International Application No. PCT/NL15/050377, dated Oct. 7, 2015, 5 pages.
Japanese Notice of Reasons for Refusal for Japanese Application No. 2017-515659, dated Feb. 28, 2019, 6 pages with English translation.
Japanese Notice of Reasons for Refusal for Japanese Application No. 2017515659, dated Mar. 6, 2019, 6 pages with English Translation.
Japanese Search Report for Japanese Application No. 2017-515659, dated Feb. 28, 2019, 27 pages with English Translation.
Kabat et al., "Sequences of Proteins of Immunological Interest," 4th ed. (1987), Bethesda, Md., National Institutes of Health.
Larson et al., "Structure/Function Analyses of Recombinant Variants of Human Factor Xa:? Factor Xa Incorporation into Prothrombinase on the Thrombin-Activated Platelet Surface Is Not Mimicked by Synthetic Phospholipid Vesicles," Biochemistry 1998, 37, 14, 5029-5038.
Lauritzen et al., Blood, 2005, 106:2149, Abstract 607A-608A).
Lee et al., "A proposed ternary complex model of prothrombinase with prothrombin: protein-protein docking and molecular dynamic simulations," J Thromb Haemost 2011; 9: 2123-6.
Levi, "Comparison of three-factor and four-factor prothrombin complex concentrates regarding reversal of the anticoagulant effects of rivaroxaban in healthy volunteers," J Thromb Haemost 2014; 12: 1428-36.
Messier et al., Blood Coagulation and Fibrinolysis 1996, 7:5-14).
Padlan, "A possible procedure for reducing the immunogenicity of antibody variable domains while preserving their ligand-binding properties," (1991) Mol. Immunol. 28:489-498.
PCT International Search Report, PCT/NL2015/050377 dated Oct. 10, 2015.
PCT Written Opinion PCT/NL2015/050377 dated Oct. 10, 2015.
Perzborn, "In vitro and in vivo studies of the novel antithrombotic agent BAY 59-7939—an oral, direct Factor Xa inhibitor," J. Thromb. Haemost. 2005, 3:514-521.
Pinto et al., "Discovery of 1-(4-Methoxyphenyl)-7-oxo-6-(4-(2-oxopiperidin-1-yl)phenyl)-4,5,6,7-tetrahydro-1H-pyrazolo[3,4-c]pyridine-3-carboxamide (Apixaban, BMS-562247), a Highly Potent, Selective, Efficacious, and Orally Bioavailable Inhibitor of Blood Coagulation Factor Xa," J. Med. Chem. 2007, 50, 22, 5339-5356.
Rao V S et al: "Group D prothrombin activators from snake venom are structural homologues of mammalian blood coagulation factor Xa". Biochemical Journal. Portland Press Ltd. GB. vol. 369. No. Pt 3. Oct. 28, 2002 (Oct. 28, 2002). pp. 635-642. XP002350493. ISSN: 0264-6021. DOI: 10.1042/BJ20020889 figure 5.
Rao[ V ] S etal, Group D prothrombin activators from snake venom are structural homologues of mammalian blood coagulation factor Xa., Biochem J., Feb. 1, 2003, 369 (Pt 3), 635-642.
Reza et al. "Molecular evolution caught in action: gene duplication and evolution of molecular isoforms of prothrombin activators in *Pseudonaja textilis* (brown snake)" J. Thrombosis and Haemostasis 4:1346-1353. (Year: 2006).
Roehrig et al., "Discovery of the Novel Antithrombotic Agent 5-Chloro-N-({(5S)-2-oxo-3-[4-(3-oxomorpholin-4-yl)phenyl]-1,3-oxazolidin-5-yl}methyl)thiophene-2-carboxamide (BAY 59-7939): An Oral, Direct Factor Xa Inhibitor," J. Med. Chem. Sep. 22, 2005; 48(19):5900-5908.
Sarkar et al., "Solubilization and Humanization of Paraoxonase-1" Journal of Lipids 2012, Article ID 610937, pp. 1-13.
Search Report for Japanese Application No. 2017-515659, dated Feb. 19, 2019, 27 pages with English Translation.
Siegal et al., "How I treat target-specific oral anticoagulant-associated bleeding," Blood 2014, 123:1152-1158.
Verhoef et al. "126 Engineered Factor Xa Variants Retain Procoagulant Activity Independent of Direct Factor Xa-Inhibitors" American Society of Hematology 57th Annual Meeting. Orlando, FL Dec. 5-8, 2015. (Year: 2015).
Verhoef et al., "Functional implications of the unique disulfide bond in venom factor V from the Australian common brown snake *Pseudonaja textilis,*" *Pseudonaja textilis*, Toxin Reviews, 33:1-2, 37-41, DOI: 10.3109/15569543.2013.844712.
Verhoef et al., Engineered factor Xa variants retain procoagulant activity independent of direct factor Xa inhibitors, Nature Communications, Sep. 13, 2017, pp. 1-10, vol. 8, No. 528, DOI: 10-1038/s41467-017-00647-9.
Chen et al., "Advance in the Development of Factor Xa Inhibitors," Evaluation and Analysis of Drug-Use in Hospitals of China, vol. 21, No. 6, (Dec. 31, 2013), pp. 655-659.
Chinese First Office Action for Chinese Application No. 201580039023.6, dated Nov. 5, 2019, 14 pages with translation.
Japanese Decision to Grant a Patent for Japanese Application No. 2017-515659, dated Nov. 26, 2019, 5 pages with English Translation.
Chinese Second Office Action for Chinese Application No. 201580039023, dated Jun. 22, 2020, 11 pages with English translation.
Korean Notification of Reason for Refusal for Korean Application No. 10-2016-7033773, dated Jul. 23, 2020, 9 pages with English Translation.
UniProtKB—Q1L658 (FA102_PSETE), "F10—Coagulation Factor X isoform 2 precursor".
Chinese Third Office Action for Chinese Application No. 201580039023, dated Feb. 20, 2021, 10 pages with translation.
Chuang et al. "Heparin Enhances the Specificity of Antithrombin for Thrombin and Factor Xa Independent of the Reactive Center Loop Sequence" The Journal of Biological Chemistry, vol. 276, No. 18, Issue of May 4, pp. 14961-14971(Feb. 2001).
Eurasian Search Report received for EA Application No. 202190813, dated Nov. 1, 2021 1 page.

(56) References Cited

OTHER PUBLICATIONS

Lu et al. "A specific antidote for reversal of anticoagulation by direct and indirect inhibitors of coagulation factor Xa" Nature Medicine, vol. 19, No. 4, 9 pages (Apr. 2013).

* cited by examiner

FIG. 8A

FIG. 8B

```
YDIAVLRLKTPITFRMNVAPACLPERDWAESTLMTQKTGIVSGFGRTHEKGRQSTLRKMLEVPYVDRNSCKLSSSFIITQMFCAGYDTK    410
YDIAVLRLKTPITFRMNVAPACLPQKDWAESTLMTQKTGIVSGFGRTHEKGRQSNILKMLEVPYVDRNTCKLSTSFSITQMMFCAGYTEAK   407
YDIAVIKLEAINFTENIIPACIPDPEFADQVLMNEFDAMSGFGRIHERGRQASTLQMLQVPYIKRHSCKESSTPAITEMMFCAGYFDTE    403
NDIALIKLSKPIKFTKYIIPACLEMKPAERVLMQQDDQLVSGGPGRVREGQLSSTILQALTVPYVNRAKCIESSNFKISGRMFCAGYDQE    421
NDIALIKLITKPIKYSRFILPACIPEQBFAESVLMQQSDOMISGFGRLQSNRQTSPILKRLTIPYVERRTCMESTSLRISARMFCAGYDEI    395
YDIAIIQLKTPIQFSENYVPACLPTADFANQVLMKQNFGIVSGFGRTRERGKTSNTLKVTLPYVDRHTCMLSSNPPITQMFCAGYDTL     413
YDIAIIQMKTPIQFSENYVPACLPTADFANQVLMKQDFGIVSGFGRIFEKGPKSKTLKVLKVPYVDRHTCMVSSETPITPNMFCAGYDTL   393
YDIAIIQMKTPIQFSENYVPACLPTADFANQVLMKQDFGIVSPRGIFPBRGPNSKTLKVLKVPYVDRHTCMLSSNPPITPMFCAGYDTL    397
YDIAIIRMKTPIQFSENYVPACLPTADFANBVLMKQDSGIVSGFGRIRFKEPTSNTLKVITPYVDRHTCMLSDPRITQMFCAGYDTL      396
 DIA     I         PAC  P    A    LM    SGFG         L       PY  R  C  S    I     MFCAG

QEDACQGDSGGPHVTRFKDTYFVTGIVSWGEGCARKGKYGITTKVTAFLKWIDRSMKTRGLPKAKSHAFEVITSSPLK              488
LEDACQGDSGGPHVTRFKNTYYVTGIVSWGEGCARKGKYGITTKVTTFLKWIDRSMEARVGPTAET  PRTA  GPPN              481
VKDACQGDSGGPHVTPFKGTYFVTGIVSWGEGCARKGKFGVTTKVSKLHRWLKGVLKKNQV                               464
EKDACQGDSGGPHVTPFKDNTWFITGVVKLGRRVRAQ     GE      IRRLAHTGLQIHHVDQ                          474
AKDACQGDSGGPHVTRKYRSTYFITGIVSWEGCAQKGKYGVTTQVSKYIRWIRDGINTLIPKGQSTRLKRHVGPIRRIVG             475
PQDACQGDSGGPHITTAYRDTHPFITGIVSWGEGCAQTGKYGVTTKVSKFILMIKRIIRQKQPSTESSTGRL                    483
PRDACQGDSGGPHTTVYRDTHPFITGIVSSGEGCARNGKYGIYTKLSKFIPWIKRIMRQKLPSTESSTGRL                     463
PQDACQGDSGGPHITAYRDTHPFITGIVSWGEGCARKGRYGIYTKLSKFIPWI                                        449
PQDACQGDSGGPHITAYRDTHPFITGIISWGEGCARKGKYGVTTKVSRFIPWIKKIMSLK                                 455
 DACQGDSGGPH   T    T     TG     G                   G
```

FIG. 8C

```
99hFXhX-HH          NRFTK          ET    9Y HH
c-FX A: -HH    -    KKFVPPKKSQEFYEKFDLAA  -  Y HH
c-FXX hX -HH   -    KKFVPPNYYYV-HQNFDLAA  -  Y HH
c-FXXchX -HH   -    KKFVPPQKAYK----FDLAA  -  Y HH
```

FIG. 9

PROHEMOSTATIC PROTEINS FOR THE TREATMENT OF BLEEDING

CROSS-REFERENCE TO RELATED APPLICATIONS

This application is a continuation of co-pending U.S. patent application Ser. No. 15/313,881, filed Nov. 23, 2016, which claims the benefit under 35 U.S.C. § 371 of International Patent Application PCT/NL2015/050377, filed May 26, 2015, designating the United States of America and published in English as International Patent Publication WO 2015/183085 A1 on Dec. 3, 2015, which claims the benefit under Article 8 of the Patent Cooperation Treaty to European Patent Application Serial No. 14169895.1, filed May 26, 2014, the contents of the entirety of each of which are hereby incorporated by this reference.

TECHNICAL FIELD

This disclosure is in the field of medical treatment. In particular, the disclosure is in the field of treating, preventing or ameliorating bleeding complications resulting from a modulated hemostatic response.

BACKGROUND

Millions of patients worldwide require anticoagulant drugs for the prophylactic management of stroke in atrial fibrillation or prevention and treatment of venous thrombosis. Prophylaxis is traditionally centered on the coumarin-based oral anticoagulant Vitamin K Antagonists (VKAs) such as Warfarin, Acenocoumarol and Phenprocoumon, which block the synthesis of vitamin K-dependent blood coagulation factors. Further anticoagulant drugs include target-specific anticoagulants, such as dabigatran, that inhibit the enzyme thrombin, which is a serine protease that converts soluble fibrinogen into insoluble strands of fibrin. Efficacious reversal of the anticoagulant effect, with a so-called antidote, is a prerequisite for safe drug usage. This is particularly important considering that, just in the Netherlands alone, over 10,000 patients treated with anticoagulants annually suffer from an adverse severe bleeding event, including up to 2,000 fatalities (H. Adriaansen, et al., "Samenvatting Medische Jaarverslagen van de Federatie van Nederlandse Trombosediensten," 2011; 1-44).

Currently available anticoagulant-antidote pairs to prevent over-anticoagulation are heparin-protamine and warfarin-vitamin K. Prothrombin complex concentrates (PCC) containing vitamin K-dependent coagulation factors II, IX, X (3-factor PCC) or II, VII, IX, X (4-factor PCC) and varying amounts of proteins C and S have been indicated for the reversal of warfarin-related effects (see, for example, Frumkin, Ann. Emerg. Med. 2013, 62:616-626). Fresh frozen plasma and recombinant factor VIIa (rfVIIa) have also been used as non-specific antidotes in patients under low molecular weight heparin treatment, suffering from major trauma or severe hemorrhage (Lauritzen et al., Blood 2005, 106:2149, Abstract 607A-608A). Also reported are pro-tamine fragments (U.S. Pat. No. 6,624,141) and small synthetic peptides (U.S. Pat. No. 6,200,955) as heparin or low molecular weight heparin antidotes; and thrombin muteins (U.S. Pat. No. 6,060,300) as antidotes for thrombin inhibitors. Prothrombin intermediates and derivatives have been reported as antidotes to hirudin and other thrombin inhibitors (U.S. Pat. Nos. 5,817,309 and 6,086,871). Despite the absence of solid clinical data, dabigatran-associated severe bleeding is preferably treated with the non-specific reversal agent activated prothrombin complex concentrate (APCC) (Siegal et al., Blood 2014, 123:1152-1158).

Newly developed direct factor Xa (FXa) inhibitors (DFXIs), such as rivaroxaban, apixaban and edoxaban, are anticoagulants and may largely replace the classic VKAs in the near future because of their rapid therapeutic effectiveness, ease of dosing and lack of monitoring requirements due to fewer drug and food interactions and predictable pharmacokinetics. DFXIs are small compound inhibitors that have been specifically designed to tightly bind to and halt the activity of blood coagulation FXa. Coagulation FXa is an essential serine protease that normally circulates as an ~60 kDa inactive precursor (zymogen) coagulation factor X (FX) in blood, but is converted upon vascular damage to its active protease form in a complex series of protein activation steps, collectively known as the blood coagulation cascade. Central to this system is the formation of the cofactor-protease complex known as the prothrombinase complex that consists of coagulation FXa in association with the cofactor factor Va (FVa), which assemble exclusively on a negatively charged phospholipid membrane and convert inactive prothrombin into the active serine protease thrombin.

A major drawback to the use of the DFXIs is the absence of a specific and adequate reversal strategy to prevent and stop potential life-threatening bleeding complications associated with its anticoagulant therapy.

Since DFXIs inhibit both free and prothrombinase-bound coagulation FXa (European Medicines Agency, 2008, CHIMP assessment report for Xarelto, Procedure No. EMEA/H/C/000944, Doc.Ref.: EMEA/543519/2008), effective restoration of normal hemostasis would, therefore, require either full replacement of circulating coagulation FXa or effective removal of inhibitory compounds from blood.

Currently, there are no specific reversal strategies available to prevent and stop potential life-threatening bleeding complications associated with DFXI therapy. Next to life-supporting and surgical therapies, non-specific reversal therapy using 3- and 4-factor PCC may be considered based on limited evidence (Siegal et al., Blood 2014, 123:1152-1158; Levi et al., J. Thrombosis Haemostatis 2014, Published online 8 May 2014; doi: 10.1111/jth.12599). A reversal strategy specific for DFXI-associated bleeding is in development, which is based on a catalytically inactive form of recombinant FXa (andexanet alpha) that serves as a decoy for DFXIs by binding and thereby trapping circulating DFXIs, thereby enabling endogenous coagulation FXa to normally participate in coagulation (Lu et al., Nature Medicine 2013, 19:446). A downside to this approach is that high doses of andexanet alpha need to be administered since stoichiometric concentrations are required to attain inhibition (400 mg IV bolus in phase III trial; Portola News Release Mar. 19, 2014). Furthermore, since the half life of DFXI partially depends on renal clearance, the amount of decoy FXa required to trap all circulating inhibitory molecules may even be higher in the case of renal failure. This reversal strategy does not provide a fast and direct procoagulant response, as the response is dependent on the generation of free, endogenous coagulation FXa.

At this moment, a direct, adequate reversal strategy to prevent and stop potential life-threatening bleeding complications associated with DFXI anticoagulant therapy is not available.

BRIEF SUMMARY

This disclosure solves this problem by providing, as an adequate reversal strategy to prevent and stop potential life-threatening bleeding complications associated with DFXI anticoagulant therapy, a recombinant protein comprising, or consisting of, a mammalian, preferably primate, more preferably human, coagulation FXa polypeptide, the polypeptide having an alteration in a region of amino acid residues corresponding to the region of amino acid residues between Gly-289 and Asp-320 of SEQ ID NO:1, preferably between Glu-297 and Asp-320 of SEQ ID NO:1, more preferably between Val-305 and Asp 320 of SEQ ID NO:1 and most preferably between His-311 and Asp-320 or between His-311 and Tyr-319 of SEQ ID NO:1, wherein the alteration is an insertion and/or replacement and/or deletion of at least one amino acid residue, preferably an insertion of at least one amino acid residue. For clarification purposes, the amino acid residue numbering is based on the human coagulation FX amino acid sequence as provided in SEQ ID NO:1.

It was found that a catalytically active human coagulation FXa, with an altered amino acid composition at a region between the Gly and Asp corresponding to Gly 289 and Asp-320 of SEQ ID NO:1, participates in the coagulation cascade as a procoagulant, whereby the factor has a decreased sensitivity to inhibition by DFXIs, compared to a coagulation FXa not having the altered amino acid composition. This disclosure provides, therefore, a procoagulant antidote that does not depend on the generation of free, endogenous coagulation FXa and offers a fast and direct reversal strategy to prevent and stop complications associated with DFXI anticoagulant therapy.

The amino acid sequence of human coagulation FX is provided in SEQ ID NO:1 and can be found in GEN-BANK® under "AAH46125.1". The amino acid residue numbering in this sequence is based on the human coagulation FX sequence. Coagulation FX with the sequence listed in SEQ ID NO:1 is a precursor containing a prepro-leader sequence (amino acid residues 1 to 40 of SEQ ID NO:1), followed by sequences corresponding to a coagulation FX light chain (amino acid residues 41 to 179 of SEQ ID NO:1), a RKR triplet (amino acid residues 180 to 182 of SEQ ID NO:1) which is removed during secretion of coagulation FX, and a coagulation FX heavy chain (amino acid residues 183 to 488 of SEQ ID NO:1) containing the activation peptide (AP) (amino acid residues 183 to 234 of SEQ ID NO:1) and the catalytic serine protease domain (amino acid residues 235 to 488 of SEQ ID NO:1).

Maturation of human coagulation FX involves inter alia proteolytic cleavage and post-translational modification in the Golgi apparatus. The mature FX protein is a two-chain molecule, composed of a light chain and a heavy chain that are linked by a disulfide bond (Uprichard et al., Blood Reviews 2002, 16:97-110). Mature human coagulation FX is activated by cleavage of a peptide bond on the heavy chain between Arg 234 and Ile-235 of SEQ ID NO:1, thereby releasing a 52-residue activation peptide from the heavy chain of coagulation FX. The resulting disulfide-linked light chain and truncated heavy chain constitute an activated FXa polypeptide.

The amino acid sequence of the light chain of human coagulation FXa is provided in SEQ ID NO:2. The amino acid sequence of the heavy chain of human coagulation FXa is provided in SEQ ID NO:3.

The term "recombinant," as used herein, refers to a protein that is produced using recombinant DNA techniques known to the person skilled in the art. A recombinant coagulation FX or FXa polypeptide is also indicated as rFX or rFXa. A recombinant protein preferably is not identical to a native protein, for example, because the amino acid composition differs and/or because of a difference in post-translational modification such as glycosylation.

The term "alteration," as used herein, refers to an insertion and/or replacement and/or deletion of at least one amino acid residue. The alteration preferably is an insertion of at least one amino acid.

The phrase "recombinant protein comprising a coagulation FXa polypeptide," as used herein, is meant to encompass a protein that comprises a recombinant coagulation FXa polypeptide, preferably mammalian, more preferably primate, and most preferably of human origin. The phrase includes, for example, a recombinant mammalian precursor protein, such as human coagulation FX, that is processed and/or activated into a mammalian coagulation rFXa polypeptide. Thus, a protein of the disclosure is preferably a recombinant mammalian, preferably primate, more preferably human coagulation FX, having an insertion and/or replacement and/or deletion, preferably an insertion, of at least one amino acid residue in a region of amino acid residues corresponding to the region of amino acid residues between Gly-289 and Asp-320 of SEQ ID NO:1, preferably between Glu-297 and Asp-320 of SEQ ID NO:1, more preferably between Val-305 and Asp-320 of SEQ ID NO:1 and most preferably between His-311 and Asp-320 of SEQ ID NO:1. In addition, the phrase includes a protein that comprises one or more additional amino acid sequences, besides the coagulation rFXa polypeptide, for example, an amino acid sequence that constitutes a tag, for example, a FLAG tag as described in EP0150126, and/or one or more other identification peptides.

In one embodiment, therefore, a recombinant protein comprising a coagulation FXa polypeptide according to the disclosure is a coagulation factor X polypeptide, the polypeptide having an alteration in a region of amino acid residues corresponding to the region of amino acid residues between Gly-289 and Asp-320, preferably between His-311 and Asp-320 of SEQ ID NO:1; wherein the alteration is an insertion of at least one amino acid residue.

The term "coagulation FX," as used herein, refers to an inactive coagulation FX precursor protein. The skilled person knows that coagulation FX is also referred to as preproprotein FX. As is used herein, a coagulation FX comprises a coagulation FXa polypeptide.

The term "mature coagulation FX," as used herein, refers to an inactive coagulation FX protein that is composed of a light chain and a heavy chain that are linked by a disulfide bond. This FX protein is also referred to as proprotein FX, or zymogen FX. As is used herein, a mature coagulation FX comprises a coagulation FXa polypeptide.

A protein of the disclosure preferably comprises, or is, a mammalian, preferably primate, more preferably human or humanized, coagulation FXa polypeptide, having an insertion and/or replacement and/or deletion, preferably an insertion, of at least one amino acid residue in a region of amino acid residues corresponding to the region of amino acid residues between Gly-289 and Asp-320 of SEQ ID NO:1.

The term "humanized," as is used herein, refers to the replacement or humanization of preferably exterior amino acid residues of a protein of one species for amino acid residues that are present in a human homologue of the protein so that the proteins of the first species will not be immunogenic, or are less immunogenic, when applied to a human. The replacement of exterior residues preferably has little, or no, effect on the interior domains, or on the interdomain contacts between light and heavy chains. A protein of the disclosure of non-human origin, preferably mammalian origin, more preferably primate origin, is preferably humanized in order to reduce the immunogenicity of the protein in a human.

A non-human protein of the disclosure preferably comprises a humanized mammalian, more preferably a humanized primate, coagulation FXa polypeptide, as the risk of an antigenic response upon administration in the human body is expected to be lower as compared to a protein of the disclosure comprising a non-humanized coagulation FXa polypeptide.

In the context of humanizing proteins, attention can be paid to the process of humanizing that is applicable to antibodies. This process makes use of the available sequence data for human antibody variable domains compiled by Kabat et al., "Sequences of Proteins of Immunological Interest," 4th ed. (1987), Bethesda, Md., National Institutes of Health, updates to this database, and other accessible U.S. and foreign databases (both nucleic acid and protein). Non-limiting examples of the methods used to generate humanized antibodies include EP 519596; U.S. Pat. No. 6,797,492; and described in Padlan et al., *Mol. Immunol.* 1991, 28:489-498. Further exemplifying the process of humanization of non-human proteins, Sarkar et al., "Journal of Lipids" 2012, Article ID 610937, p. 1-13, described that Paraoxonase-1 was successfully humanized by altering the surface of the enzyme to reflect the human sequence.

The term "coagulation FXa polypeptide" refers to the catalytically active form of a coagulation FX. The coagulation FXa polypeptide is obtained by cleavage of the activation peptide from the heavy chain of a mature coagulation FX. A coagulation FXa polypeptide activates prothrombin and, as a result, promotes coagulation. In the context of the disclosure, a protein is a coagulation FXa polypeptide if it is a procoagulant serine protease and if the full-length amino acid sequence of the protein comprises stretches of, or single, amino acid residues that correspond to stretches of, or single, amino acid residues that are conserved between coagulation FX factors of different species, as is indicated in FIGS. 8A-8C. For example, a procoagulant serine protease comprising a polypeptide that contains stretches of amino acid residues that correspond to amino acid residues Cys-246 to Ala-250, Phe-260 to Leu-266 and/or Asp-413 to His-423 of SEQ ID NO:1, is assumed to be a coagulation FXa polypeptide. The coagulation FXa polypeptide is preferably obtained by local and/or topical application of a recombinant protein according to the disclosure. Methods to determine whether a protein is a serine protease are known in the art and include sequence comparison and use of a protease detection kit, for example, from Sigma-Aldrich.

The term "mammalian coagulation FXa polypeptide," as used herein, refers to a coagulation FXa polypeptide that is endogenously present in a mammal, preferably a primate, more preferably a human.

The term "coagulation inhibitor," as used herein, refers to an anti-coagulation agent. The term "coagulation inhibitor" includes, but is not limited to: (i) agents, such as heparin, that stimulate the activity of antithrombin, (ii) coumarin-based oral anticoagulant vitamin K antagonists, such as warfarin, acenocoumarol and phenprocoumon, and (iii) DFXIs.

The term "DFXI," as used herein, refers to direct FXa inhibitors, for example, oral direct FXa inhibitors. DFXIs are small compound inhibitors that bind to and halt the activity of coagulation FXa. The group of DFXIs includes, but is not limited to, rivaroxaban (5-chloro-N-[[(5S)-2-oxo-3-[4-(3-oxo-4-morpholinyl)phenyl]-5-oxazolidinyl] methyl]-2-thiophenecarboxamide), apixaban (1-(4methoxyphenyl)-7-oxo-6-[4-(2-oxopiperidin-1-yl)phenyl]-4,5,6,7-tetrahydro-1H-pyrazolo[3,4-c]pyridine-3-carboxamide), edoxaban (N'-(5-chloropyridin-2-yl)-N-[(1S,2R,4S)-4-(dimethylcarbamoyl)-2-[(5-methyl-6,7-dihydro-4H-[1,3]thiazolo[5,4-c]pyridine-2-carbonyl)amino]cyclohexyl]oxamide; 4-methylbenzenesulfonic acid), betrixaban (N-(5-chloropyridin-2-yl)-2-[[4-(N,N-dimethylcarbamimidoyl) benzoyl]amino]-5-methoxybenzamide), darexaban (N-[2-[[4-(Hexahydro-4-methyl-1H-1,4-diazepin-1-yl)benzoyl] amino]-3-hydroxyphenyl]-4-methoxybenzamide), otamixaban (methyl (2R,3R)-2-[(3-carbamimidoylphenyl) methyl]-3-[[4-(1-oxidopyridin-1-ium-4-yl)benzoyl]amino] butanoate), eribaxaban (2R,4R)-1-N-(4-chlorophenyl)-2-N-[2-fluoro-4-(2-oxopyridin-1-yl)phenyl]-4-methoxypyrrolidine-1,2-dicarboxamide), letaxaban (1-[1-[(2 S)-3-(6-chloronaphthalen-2-yl)sulfonyl-2-hydroxypropanoyl]piperidin-4-yl]-1,3-diazinan-2-one, LY517717 (N-[2-[4-(1-methylpiperidin-4-yl)piperazin-1-yl]-2-oxo-1-phenylethyl]-1H-indole-6-carboxamide) and 813893 (N-cyclohexyl-N-[2-[(4-methyl-1,3-thiazol-2-yl) amino]-2-oxoethyl]furan-2-carboxamide). The terms "DOAC" (direct oral anticoagulant) and "DFXI" are used interchangeably herein.

The term "homologous," as used herein, refers to amino acid sequence identity between two amino acid sequences, expressed as a percentage of the total length of the two amino acid sequences. Sequence identity is determined by comparing the identity of individual amino acid residues of an amino acid sequence to the corresponding amino acid residue in another amino acid sequence.

The term "region," as used herein, refers to a stretch of amino acid residues that is bordered by two amino acid residues. The numbering of amino acid residues as applied herein is based on the amino acid sequence of SEQ ID NO:1.

The term "insertion" or "inserted," as used herein, refers to the addition of amino acid residues in a specific region of a native coagulation FXa polypeptide, thereby increasing the number of amino acid residues in the region, compared to the number of amino acid residues in that region of the native coagulation factor FXa polypeptide.

The term "replacement" or "replaced," as used herein, refers to the substitution of one or more amino acid residues in a specific region, or at a specific site, of a coagulation factor Xa polypeptide, thereby altering the amino acid sequence, but not the number of amino acid residues in the region. A replacement is the consequence of the deletion of an amino acid residue followed by the insertion of a different amino acid residue at the same position.

The term "deletion" or "deleted," as used herein, refers to deleting one or more amino acid residues in a specific region, or at a specific site, of a coagulation factor Xa polypeptide, thereby reducing the number of amino acid residues in the region of the polypeptide.

The term "native coagulation FXa polypeptide," as used herein, refers to an endogenous coagulation FXa polypeptide that naturally occurs in an animal, preferably in a mammal, more preferably in a primate, more preferably in a human.

The term "amino acid composition," as used herein, refers to the amino acid sequence and length of a stretch of amino acid residues, wherein the length is determined by the number of amino acid residues in that stretch.

The insertion, replacement and/or deletion, preferably insertion, of one or more amino acid residues can be performed using recombinant DNA techniques that are well known to the person skilled in the art. For example, the person skilled in the art can use synthetic DNA, PCR technology and molecular cloning to obtain recombinant DNA constructs having a DNA sequence encoding a protein of this disclosure. Suitable methods and means are described in Green and Sambrook, *Molecular Cloning: A Laboratory Manual*, CSHL Press, 2012.

The phrase "corresponding to the region of amino acid residues between," for example, with regard to the region of amino acid residues corresponding to the region of amino acid residues between His-311 and Asp-320 of SEQ ID NO:1, is used herein to indicate that the residue number of the conserved His and Asp residues of another coagulation FXa corresponding to the His-311 and Asp-320 of SEQ ID NO:1, may differ from the residue number attributed to the His and Asp residue in SEQ ID NO:1 (see FIGS. 8A-8C). Differences in amino acid residue numbers can, for example, be the result of a different way of numbering amino acid residues. Also, a difference in amino acid residue number can be the result of a difference in length of a coagulation FXa polypeptide as compared to the length of the human coagulation FXa polypeptide that is indicated in FIGS. 8A-8C. Similarly, the amino acid residues Gly-289, Glu-297, Val-305 and Tyr-319, of SEQ ID NO:1, are conserved between coagulation FXa polypeptides of different species (see FIGS. 1 and 8A-8C). It is, therefore, possible to identify amino acid residues that correspond to the amino acid residues in another coagulation FXa polypeptide. The person skilled in the art will, therefore, understand that the amino acid residue numbering as applied herein is not limiting for the disclosure, but is only applied for clarity purposes.

The skilled person will know how to identify a region of amino acid residues that corresponds to the region of amino acid residues between the conserved amino acid residues of SEQ ID NO:1 that border a region as described herein. When the amino acid residues 289-322 of SEQ ID NO:1 are aligned with the corresponding amino acid residues in coagulation FXa polypeptides of different species, it is to be concluded that the amino acid residues at positions 289, 297, 305, 311, 313, 314, 318, 319, 320, and 322 of SEQ ID NO:1 are conserved, though not identical, in coagulation FXa polypeptides of different species, especially in mammals, wherein Asp-322 of SEQ ID NO:1 is a highly conserved catalytic residue (Asp-102 in chymotrypsinogen numbering; Bode et al., *EMBO Journal* 1989, 8:3467-3475; Messier et al., *Blood Coagulation and Fibrinolysis* 1996, 7:5-14 and FIGS. 1, 8A, 8B and 8C).

Due to the highly conserved nature of the region of amino acid residues in and around Gly-289 and Asp-320 of SEQ ID NO:1, or in and around the corresponding Gly and Asp residues in a non-human coagulation FXa, the person skilled in the art is able to identify a region of amino acid residues corresponding to the region of amino acid residues between Gly-289 and Asp-320 of SEQ ID NO:1. The same general principle applies to other amino acid residues that border a region as described herein. In other words, the conserved nature of specific amino acid residues will give the skilled person an unambiguous pointer as to which amino acid residues constitute a region.

A person skilled in the art will understand that this disclosure relates to the amino acid composition of a region of amino acid residues corresponding to the region of amino acid residues between Gly-289 and Asp-320, most preferably between His-311 and Asp-320 of SEQ ID NO:1. Therefore, the person skilled in the art will understand that the amino acid sequence of the remainder of a protein of the disclosure can vary, under the condition that the protein remains a, or is activated into a, procoagulant FXa polypeptide with decreased sensitivity to DFXIs. The remainder of a protein of the disclosure may thus vary as it, for example, varies between coagulation FX, or coagulation FXa, polypeptides of different species.

The number of amino acid residues in a region corresponding to the region between Gly-289 and Asp-320, preferably between His-311 and Asp-320 of SEQ ID NO:1 is conserved between coagulation FX proteins of different species, especially between species belonging to the group of mammals or to the group of primates. This region is also present in zymogen FX protein and FXa polypeptide. Hence, the number of amino acid residues is also conserved in zymogen FX protein and FXa polypeptide and in the corresponding region of zymogen FX protein and FXa polypeptide. The conserved number of amino acid residues in a region of amino acid residues corresponding to the region between Gly-289 and Asp-320 of SEQ ID NO:1 is thirty, not including Gly-289 and Asp-320. The conserved number of amino acid residues in a region of amino acid residues corresponding to the region between His-311 and Asp-320 of SEQ ID NO:1 is eight, not including His-311 and Asp-320.

It was found that the insertion and/or replacement and/or deletion, preferably the insertion, of at least one amino acid residue in a region of amino acid residues corresponding to the region of amino acid residues between Gly-289 and Asp-320, preferably between His-311 and Asp-320 of SEQ ID NO:1 in a protein of the disclosure, yields a catalytically active coagulation FXa with decreased sensitivity to inhibition by DFXIs.

Tyr-319 of human FXa has been demonstrated to be a DFXI-coordinating residue (Roehrig et al., *J. Med. Chem.* 2005, 48:5900-5908; Pinto et al., *J. Med. Chem.* 2007, 50:5339-5356), while Asp-322 of SEQ ID NO:1 is present in the catalytic serine protease site (Messier et al., *Blood Coagulation and Fibrinolysis* 1996, 7:5-14). Without being bound by theory, it is possible that the close proximity of an altered amino acid residue, such as an insertion of at least one amino acid residue, in the region between Gly-289 and Asp-320 to the DFXI-coordinating residue Tyr-319 of SEQ ID NO:1, or the corresponding tyrosine, and/or the close proximity to the catalytic domain is responsible for the decreased sensitivity for a DFXI. It is found that the region of amino acid residues corresponding to the region of amino acid residues between Gly-289 and Asp-320 of SEQ ID NO:1 in a protein of the disclosure can be altered in amino acid residue number and in amino acid sequence, thereby generating a catalytically active coagulation FXa with decreased sensitivity for DFXIs.

The alteration is selected from an insertion, a replacement and/or a deletion, and preferably is an insertion, more preferably an insertion combined with an alteration of at least one amino acid in the region between Gly-289 and Asp-320 of SEQ ID NO:1.

Particularly preferred is a protein of the disclosure wherein the insertion is 1-50, preferably 1-20, amino acid residues. The insertion in a region of amino acid residues corresponding to the region of amino acid residues between Gly-289 and Asp-320, preferably between His-311 and Asp-320, of SEQ ID NO:1 in a protein of the disclosure comprises or consists of between 1-50, preferably between 1-20, amino acid residues. The insertion preferably comprises, or consists of, at least 1, 2, 3, 4, 5, 6, 7, 8, 9, 10, 11, 12, 13, 14, 15, 16, 17, 18, 19, or 20 amino acid residues, resulting in a total of 9, 10, 11, 12, 13, 14, 15, 16, 17, 18, 19, or 20, 21, 22, 23, 24, 25, 26, 27, or 28, respectively, amino acids between His-311 and Asp-320. Particularly preferred is the insertion of at least five amino acid residues, such as an insertion of 9, 12 or 13 amino acid residues. The person skilled in the art will understand that the amino acid residues can be inserted at any position in a region of amino acid residues corresponding to the region of amino acid residues between Gly-289 and Asp-320 of SEQ ID NO:1. An amino acid residue suitable for insertion is selected from the group of twenty amino acid residues as listed in Table 1. The person skilled in the art will understand that the inserted amino acid residues may undergo a post-translational chemical alteration in vivo or in vitro. As is indicated herein above, the person skilled in the art can use synthetic DNA, PCR technology and molecular cloning to obtain recombinant DNA constructs having a DNA sequence encoding a protein of this disclosure having an insertion of between 1-50 amino acid residues in the region of amino acid residues corresponding to the region between Gly-289 and Asp-320 of SEQ ID NO:1.

The insertion in a region of amino acid residues corresponding to the region of amino acid residues between Gly-289 and Asp-320 of SEQ ID NO:1 in a protein of the disclosure is preferably between Thr-315 and Lys-316, between Lys-316 and Glu-317, between Glu-317 and Thr-318, and/or between Thr-318 and Tyr-319 of SEQ ID NO:1 or between two amino acid residues corresponding to these amino acid residues in a non-human coagulation FXa polypeptide.

Particularly preferred is a protein of the disclosure wherein the replacement is 1-30, preferably 1-8, more preferably 6 or 7, amino acid residues. The replacement of amino acid residues in a region of amino acid residues corresponding to the region of amino acid residues between Gly-289 and Asp-320 of SEQ ID NO:1 in a protein of the disclosure preferably comprises, or consists of, between 1-30 amino acid residues in a region corresponding to the region of amino acid residues between Gly-289 and Asp-320 of SEQ ID NO:1. The replacement preferably comprises, or consists of, 1, 2, 3, 4, 5, 8, 9, 10, 11, 12, 13, 14, 15, 16, 17, 18, 19, 20, 21, 22, 23, 24, 25, 26, 27, 28, 29 or 30 amino acid residues. It is preferred that conserved amino acid residues such as, for example, Glu-297, Val-305 and/or His-311 as indicated in SEQ ID NO:1 are not replaced. Particularly preferred is the replacement of either six or seven amino acid residues.

An amino acid residue present in a region corresponding to the region of amino acid residues between Gly-289 and Asp-320 of SEQ ID NO:1 of a protein of the disclosure is preferably replaced by any one of the amino acid residues listed in Table 1, preferably by an amino acid of the same group as is indicated in the columns "side chain polarity" and "side chain charge" in Table 1. Preferably, one or more of Asn-312, Arg-313, Phe-314, Thr-315, Lys-316, Glu-317, Thr-318 and Tyr-319 of SEQ ID NO:1, or their corresponding amino acid residues in a non-human protein of the disclosure, are replaced by any one of the amino acid residues as indicated in Table 1. Asn-312 of SEQ ID NO:1 is preferably replaced by a Thr or Lys residue. Arg-313 is preferably replaced by an amino acid residue with a basic polarity and positively charged side-chain (see Table 1), more preferably by a Lys residue. Amino acid residue Thr-315 is preferably replaced by a polar amino acid residue with a neutral side-chain or by a nonpolar amino acid residue with a neutral side-chain, more preferably by a Val residue. Lys-316 of SEQ ID NO:1 is preferably replaced by a Pro residue. Glu-317 of SEQ ID NO:1 is preferably replaced by a Val residue. Thr-318 is preferably replaced by a polar amino acid residue with a neutral side-chain or by a nonpolar amino acid residue with a neutral side-chain, more preferably by a Ser or Ala residue.

The replacement of amino acid residues in a region of amino acid residues corresponding to the region of amino acid residues between Gly-289 and Asp-320 of SEQ ID NO:1 in a protein of the disclosure preferably comprises, or consists of, at least two amino acid residues. Any combination of at least two amino acid residues is envisaged in the disclosure, for example, a replacement of Asn-312 of SEQ ID NO:1 and Lys-316 of SEQ ID NO:1 by a Pro residue and an Ala residue, respectively, or replacement of Asn-312, Arg-313, Thr-315, Lys-316, Glu-317, Thr-318 and Tyr-319 of SEQ ID NO:1 by any one of the amino acid residues listed in Table 1. Particularly preferred is a protein of the disclosure having a replacement of (i) Asn-312, (ii) Arg-313, (iii) Thr-315, (iv) Lys-316, (v) Glu-317 and (vi) Thr-318 of SEQ ID NO:1 by a (i) Thr or Pro residue, (ii) Lys residue, (iii) Val residue, (iv) Pro residue, (v) Val residue and (vi) Ser or Ala residue, respectively.

The person skilled in the art will understand that when amino acid residues are replaced in a region of amino acid residues corresponding to the region between Gly-289 and Asp-320 of SEQ ID NO:1 of a non-human protein of the disclosure, only those amino acid residues are replaced that are not already present in a preferred protein of the disclosure. The person skilled in the art will know that the aforementioned reference to SEQ ID NO:1 is only made in the context of exemplifying the replacement of amino acid residues in a specified region of amino acid residues. Therefore, the skilled person will have an indication which one or more amino acid residues they may replace in a non-human coagulation FXa for what other amino acid residue or residues.

A protein of the disclosure may further comprise a deletion of at least one amino acid residue in a region of amino acid residues corresponding to the region of amino acid residues between Gly-289 and Asp-320 of SEQ ID NO:1. Particularly preferred is a protein of the disclosure having a deletion of at least 1, 2, 3, 4, 5, 6, 7, 8, 10, 15, 20 or 30 amino acid residues.

A preferred protein of the disclosure comprises a combination of an insertion and a replacement, or a combination of an insertion, a replacement, and/or a deletion. Insertions and deletions may occur independently of each other and it is thus possible that, for example, an insertion of five amino acid residues and a deletion of five amino acids are present at different amino acid positions in a region of amino acid residues corresponding to the region of amino acid residues between Gly-289 and Asp-320 of SEQ ID NO:1, without affecting the total number of amino acid residues in a coagulation FX. The skilled person will understand that an insertion or deletion changes the amino acid residue numbering in a protein. With regard to a convenient assessment of where an alteration is located and what the alteration constitutes, the skilled person can perform a multiple alignment of the amino acid sequence of different coagulation FX proteins as shown in FIGS. 8A-8C. The skilled person can deduce from such an alignment which amino acid residues are altered. The skilled person can use conserved amino acid residues, for example, Glu-297, Val-305 and/or His-311 as markers to assess the amino acid residue number where the alteration took place.

Particularly preferred is a protein of the disclosure wherein the insertion is 1-50, preferably 1-20, amino acid residues and wherein the replacement is 1-7, preferably 6, amino acid residues. The preferred protein has an insertion of between 1-50, preferably between 1-20, amino acid residues, combined with a replacement of between 1-8, preferably either 6 or 7, amino acid residues in a region of amino acid residues corresponding to the region of amino acid residues between Gly-289 and Asp-320 of SEQ ID NO:1

A more preferred protein of the disclosure has an insertion of at least 1, 2, 3, 4, 5, 6, 7, 8, 9, 10, 11, 12, 13, 14, 15, 16, 17, 18, 19, or 20 amino acid residues and a replacement of at least 1, 2, 3, 4, 5, 6 or 7 amino acid residues in a region of amino acid residues corresponding to the region of amino acid residues between Gly-289 and Asp-320 of SEQ ID NO:1, meaning that the insertion of at least 1-20 amino acid residues is combined with a replacement of at least 1, 2, 3, 4, 5, 6 or 7 amino acid residues. The disclosure is directed to all possible combinations of the aforementioned insertion and replacement. Particularly preferred is a protein having an insertion of 12 or 13 amino acid residues and a replacement of 6 amino acid residues in a region of amino acid residues corresponding to the region of amino acid residues between Gly-289 and Asp-320 of SEQ ID NO:1.

A protein of the disclosure most preferably comprises a region of amino acid residues having the amino acid sequence of SEQ ID NO:4, SEQ ID NO:5, SEQ ID NO:9, SEQ ID NO:10 or SEQ ID NO:11 between amino acid residues corresponding to the amino acid residues His-311 and Asp-320 of SEQ ID NO:1.

Furthermore, alteration of Arg-366, Glu-369, Phe-396, Asp-413, Ala-414, Cys-415, Gln-416, Ser-419, Val-437, Ser-438, Trp-439, Gly-440, Glu-441, Gly-442, Cys-443, Gly-450, Ile-451 and Tyr-452 of SEQ ID NO:1 is likely to result in a protein that is desensitized to DFXIs. Without being bound by theory, Arg-366, Glu-369, Phe-396, Asp-413, Ala-414, Cys-415, Gln-416, Ser-419, Val-437, Ser-438, Trp-439, Gly-440, Glu-441, Gly-442, Cys-443, Gly-450, Ile-451 and Tyr-452 of SEQ ID NO:1 are likely to be DFXI-coordinating residues. Literature indirectly supports this view, as it is shown that at least some of these residues are involved in binding of DFXIs (Roehrig et al., *J. Med. Chem.* 2005, 48:5900-5908; Pinto et al., *J. Med. Chem.* 2007, 50:5339-5356). A protein of the disclosure preferably has replaced or deleted an amino acid residue corresponding to Arg-366, Glu-369, Phe-396, Asp-413, Ala-414, Cys-415, Gln-416, Ser-419, Val-437, Ser-438, Trp-439, Gly-440, Glu-441, Gly-442, Cys-443, Gly-450, Ile-451 or Tyr-452 of SEQ ID NO:1. Amino acid residues Arg-366, Glu-369, Phe-396, Asp-413, Ala-414, Cys-415, Gln-416, Ser-419, Val-437, Ser-438, Trp-439, Gly-440, Glu-441, Gly-442, Cys-443, Gly-450, Ile-451 and/or Tyr-452 of SEQ ID NO:1, or the corresponding amino acid residues in a related protein, are preferably replaced by any one of the amino acid residues as listed in Table 1. Also, a protein of the disclosure preferably has an insertion of at least one amino acid residue, such as 1, 2, 3, 4, 5, 6, 7, 8, 9, 10, 11, 12, 13, 14, 15, 16, 17, 18, 19, 20 amino acid residues in a region of amino acid residues corresponding to the region between the 15 amino acid residues located at the N-terminal and 15 amino acid residues located at the C-terminal from Arg-366, Glu-369, Phe-396, Asp-413, Ala-414, Cys-415, Gln-416, Ser-419, Val-437, Ser-438, Trp-439, Gly-440, Glu-441, Gly-442, Cys-443, Gly-450, Ile-451 and/or Tyr-452. The alteration of Phe-396, Arg-366, Glu-369, Asp-413, Ala-414, Cys-415, Gln-416, Ser-419, Val-437, Ser-438, Trp-439, Gly-440, Glu-441, Gly-442, Cys-443, Gly-450, Ile-451 and/or Tyr-452 of SEQ ID NO:1. The insertion in a region as indicated in this paragraph is preferably combined with an alteration in the region between Gly-289 and Asp-320 of SEQ ID NO:1 as defined hereinabove.

This disclosure also encompasses proteins that are substantially homologous and biologically equivalent to a protein of the disclosure. A protein of the disclosure preferably has an amino acid sequence that is more than 60%, preferably more than 70%, more preferably more than 80%, and most preferably more than 90% homologous to SEQ ID NO:1 or to the activated form thereof, wherein the protein is catalytically active (procoagulant), or catalytically active after processing/activation, and has a decreased sensitivity to DFXIs, preferably a DFXI selected from the group consisting of rivaroxaban, apixaban, edoxaban and betrixaban. The person skilled in the art knows how the preproprotein or proprotein of coagulation FX is processed to its catalytically active form. The UniProt database provides an overview, under Accession Number P00742, of the processing of human coagulation FX to activated human coagulation FXa. The skilled person will thus be able to determine which amino acid residues are present or absent in coagulation FXa.

The term "decreased sensitivity to DFXIs," as used in the context of this disclosure, refers to the concentration of a DFXI that is required to produce 50% of the maximum inhibition (Ki), that is higher for a polypeptide of this disclosure than for a native coagulation FXa, wherein the native coagulation FXa is preferably derived from blood plasma or is recombinantly produced. The Ki of a DFXI is preferably determined by pre-incubating a protein of the disclosure with 0.001 to 100 µM of a DFXI and subsequently performing an experiment wherein the catalytic activity toward Spectrozyme Xa (Sekisui Diagnostics; Stamford, Conn., USA) by peptidyl substrate conversion is assayed. The Ki of a protein of the disclosure is preferably increased more than two times, more preferably, increased between 50 and 100 times, and most preferably, increased more than 100 times as compared to the Ki of the native coagulation FXa without an alteration of at least one amino acid residue in a region of amino acid residues corresponding to the region of amino acid residues between Gly-298 and Asp-320 of SEQ ID NO:1.

It was unexpectedly found that a protein of the disclosure has an increased binding affinity for coagulation FVa, the binding partner of coagulation FXa in the prothrombinase complex, as compared to the binding affinity of native coagulation FXa for coagulation FVa. The binding affinity of a human or humanized protein of the disclosure for FVa is at least two times higher than the binding affinity of native human FXa for FVa.

Assays for determining the binding affinity are known in the art, for example, by using a binding partner (such as FVa or FXa) with a radiolabel. The amount of radiation emitted upon binding can be used to calculate the binding affinity. Also, non-radioactive methods such as surface plasmon resonance and dual polarization interferometry can be used to quantify the binding affinity from concentration-based assays but also from the kinetics of association and dissociation and, in the latter, the conformational change induced upon binding. Recently, Microscale Thermophoresis (MST), an immobilization-free method was developed, that allows the determination of the binding affinity between two proteins (Wienken et al., *Nature Communications* 2010, 1:100). Preferably, the binding affinity of the coagulation FVa-FXa complex is determined via either the kinetics of prothrombin or prothrombin derivatives (prethrombin-1, prethrombin-2) conversion (Bos et al., *Blood* 2009, 114:686-692), fluorescence intensity/anisotropy measurements (Bos et al., *J. Biol. Chem.* 2012, 287: 26342-51), or isothermal titration calorimetry (ITC).

The disclosure further provides a nucleic acid molecule comprising a DNA sequence that encodes a protein of the disclosure. The person skilled in the art will understand how to generate a DNA sequence that encodes an amino acid sequence of a protein of this disclosure and how to manufacture and isolate a nucleic acid molecule with the DNA sequence using generally known recombinant DNA techniques. The sequence of the nucleic acid molecule is preferably codon-optimized for expression in a host cell of the disclosure. In this way, codons are used that are favored for high-level expression in a specific host cell.

This disclosure also provides an expression vector comprising a nucleic acid molecule of the disclosure.

Nucleic acid molecules are preferably inserted in an expression vector using recombinant DNA techniques known by the person skilled in the art. Expression vectors in the context of the disclosure direct the expression of a protein of the disclosure in a host cell. These expression vectors are preferably replicable in a host cell, either as episomes or as part of the chromosomal DNA. Further, the expression vector preferably comprises (i) a strong promoter/enhancer, such as the CMV or SV40 promoter, (ii) an optimal translation initiation sequence, such as a ribosomal binding site and start codon, preferably a KOZAK consensus sequence and (iii) a transcription termination sequence, including a poly(A) signal when the protein is expressed in eukaryotic cells. Suitable expression vectors include plasmids and viral vectors such as adenoviruses, adeno-associated viruses and retroviruses. The person skilled in the art will understand that the expression vector to be used is dependent on the host cell that is used for expression of a recombinant protein. An expression vector of the disclosure is preferably suited for expression of a nucleic acid molecule of the disclosure in a prokaryotic cell including a bacterial cell, or, more preferred, in a eukaryotic host cell, such as a yeast cell and a mammalian cell. Particularly preferred is mammalian expression vector pCMV4.

As an alternative, a nucleic acid molecule of the disclosure may be inserted in the genome of a host cell. The insertion preferably is at a locus or within a region that ensures expression of a nucleic acid molecule of the disclosure in the host cell.

The disclosure further provides a host cell comprising a nucleic acid molecule of the disclosure. The disclosure preferably provides a host cell expressing a nucleic acid molecule of the disclosure, thereby producing a protein of the disclosure. The protein is either produced within the host cell or, preferably, secreted from the host cell.

Suitable host cells for use in this disclosure include prokaryotic and eukaryotic cells, such as bacterial cells, yeast cells, insect cells, animal cells, mammalian cells, murine cells, rat cells, sheep cells, simian cells and human cells. Examples of suitable eukaryotic host cells include, but are not limited to, HEK 293 cells, the hamster cell line CHO and BHK-21; the murine host cells NIH3T3, NSO and C127; the simian host cells COS and Vero; and the human host cells HeLa, PER.C6®, U-937 and Hep G2. Suitable cells are available from public sources such as ATCC and Life Technologies. A number of transfection techniques are known in the art, see, e.g., Graham et al., *Virology* 1973, 52:456; Green et al., *Molecular Cloning: A Laboratory Manual* 2012, CSHL Press; Davis et al., *Basic Methods in Molecular Biology* 1986, Elsevier; and Chu et al., *Gene* 1981, 13:197. The person skilled in the art preferably employs techniques as described in these references to introduce one or more exogenous nucleic acid molecules into suitable host cells.

A particularly preferred host cell for the production of a protein of the disclosure is a HEK 293 cell.

The disclosure further provides a pharmaceutical composition comprising a protein of the disclosure, or a pharmaceutically acceptable salt thereof, and a pharmaceutically acceptable carrier or excipient. A pharmaceutical composition of the disclosure preferably comprises one or more of diluents, fillers, salts, buffers, stabilizers, solubilizers, and other materials known in the art. The characteristics of the carrier will depend on the route of administration, as is known to the skilled person. To reduce the potential thrombotic risk of administering the serine protease FXa, a pharmaceutical composition of the disclosure preferably comprises a protein of the disclosure that is activated after administering to the subject.

The term "subject" refers to the group of mammals, preferably humans.

The term "pharmaceutical composition" refers, in the context of the invention, to a combination of a protein of the disclosure with a carrier, inert or active, making the composition suitable for therapeutic use in vivo or ex vivo.

The term "pharmaceutically acceptable," as used herein, refers to a nontoxic material that is compatible with the physical and chemical characteristics of a protein of the disclosure and does not interfere with the effectiveness of the biological activity of the protein.

A pharmaceutical composition of the disclosure may be adapted for enteral administration of the composition, wherein the composition is absorbed through the digestive tract, e.g., oral ingestion or rectal administration. The composition is preferably encapsulated, for example, by liposomes, to prevent proteolytic degradation.

A pharmaceutical composition of the disclosure preferably is applied locally, for example, at or in a wound or to a blood vessel, preferably an artery, that supplies the wounded region with blood. The local administration is a topical administration, for example, in the form of a cream, foam, gel, lotion or ointment, or a parenteral administration, for example, by injection or infusion, to generate a local or systemic therapeutic effect. Topical administration of a protein of the disclosure for a local effect reduces the risk of a potential systemic thrombotic incident.

A pharmaceutical composition of the disclosure, preferably comprising coagulation FX or a mature coagulation FX that comprises an altered coagulation factor Xa polypeptide, is preferably systemically administered, preferably by parenteral administration. Systemic administration of an inactive preproprotein or inactive proprotein will result in the formation of an active prothrombinase complex that consists of coagulation FXa in association with FVa on negatively charged phospholipid membranes where it converts inactive prothrombin into the active serine protease thrombin.

A pharmaceutical composition of the disclosure is preferably adapted for parenteral administration, wherein the composition is intravenously, intra-arterial, subcutaneously, and/or intramuscularly introduced. Parenteral administration involves the injection or infusion of a pharmaceutical composition of the disclosure into a body tissue or body fluid, whereby preferably a syringe, needle, or catheter is used. As an alternative, needle-less high-pressure administration may be used as means for parenteral administration.

For injectable compositions (e.g., intravenous compositions), the carrier may be aqueous or oily solutions, dispersions, emulsions and/or suspensions. Preferably, the carrier is an aqueous solution, preferably distilled sterile water, saline, buffered saline, or another pharmaceutically acceptable excipient for injection.

A pharmaceutical composition of the disclosure is preferably used in a variety of therapeutical applications. For example, the pharmaceutical composition can be used as bypassing agent in the treatment or amelioration of disorders wherein normal blood coagulation is impaired, such as in hemophilia A and B, including in hemophilia A and B inhibitor patient groups, or in factor X deficiency.

The disclosure further provides a protein according to the disclosure or pharmaceutical composition according to the disclosure for use in a method of completely or partially reversing an anti-coagulant effect of a coagulation inhibitor in a subject.

The term "anti-coagulant effect" refers to the therapeutic effect, such as the prevention of blood clotting, that is the result of the action of coagulation inhibitors.

The disclosure further provides the use of a protein of the disclosure for the manufacture of a medicament for completely or partially reversing an anti-coagulant effect of a coagulation inhibitor in a subject.

The coagulation inhibitor preferably is a direct FXa inhibitor (DFXI), more preferably a direct FXa inhibitor selected from the group formed by rivaroxaban (5-chloro-N-[[(5S)-2-oxo-3-[4-(3-oxo-4-morpholinyl)phenyl]-5-oxazolidinyl]methyl]-2-thiophenecarboxamide), apixaban (1-(4methoxyphenyl)-7-oxo-6-[4-(2-oxopiperidin-1-yl)phenyl]-4,5,6,7-tetrahydro-1H-pyrazolo[3,4-c]pyridine-3-carboxamide), edoxaban (N'-(5-chloropyridin-2-yl)-N-[(1S,2R,4S)-4-(dimethylcarbamoyl)-2-[(5-methyl-6,7-dihydro-4H-[1,3]thiazolo[5,4-c]pyridine-2-carbonyl)amino]cyclohexyl]oxamide; 4-methylbenzenesulfonic acid) and/or betrixaban (N-(5-chloropyridin-2-yl)-2-[[4-(N,N-dimethylcarbamimidoyl)benzoyl]amino]-5-methoxybenzamide).

The disclosure further provides a method of completely or partially reverting an anti-coagulant effect of a coagulation inhibitor in a subject, the method comprising administering to the subject a therapeutically effective amount of a protein of the disclosure or a pharmaceutical composition of the disclosure. Preferably, a method of the disclosure is applied for preventing or ameliorating bleeding complications that are associated with anticoagulant therapy.

The term "therapeutically effective amount" as used herein means that the amount of the active ingredient contained in the pharmaceutical composition to be administered is of sufficient quantity to achieve the intended purpose, such as, in this case, to completely or partially reverse an anti-coagulant effect of a coagulation inhibitor. The amount of active ingredient, i.e., a protein of the disclosure, in a pharmaceutical composition according to the disclosure preferably is in the range of about 50 mg to about 600 mg. A pharmaceutical composition according to the disclosure is preferably administered only once, twice or three times, preferably only once, to a subject in need of complete or partial reversal of an anti-coagulant effect of a coagulation inhibitor.

For the purpose of clarity and a concise description, features are described herein as part of the same or separate embodiments; however, it will be appreciated that the scope of the disclosure may include embodiments having combinations of all or some of the features described.

```
(human coagulation factor X protein)
                                                                    SEQ ID NO: 1
    1      mgrplhlvll  saslagllll  geslfirreq  annilarvtr  ansfleemkk  ghlerecmee 61      tcsyeearev  fedsdktnef  wnkykdgdqc  etspcqnqgk  ckdglgeytc  tclegfegkn 121      celftrklcs  ldngdcdqfc  heeqnsvvcs  cargytladn  gkaciptgpy  pcgkqtlerr 181      krsvaqatss  sgeapdsitw  kpydaadldp  tenpfdlldf  nqtqpergdn  nitrivggqe 241      ckdgecpwqa  llineenegf  cggtilsefy  iltaahclyq  akrfkvrvgd  rnteqeegge 301      avhevevvik  hnrftketyd  fdiavlrlkt  pitfrmnvap  aclperdwae  stlmtqktgi 361      vsgfgrthek  grqstrlkml  evpyvdrnsc  klsssfiitq  nmfcagydtk  qedacqgdsg 421      gphvtrfkdt  yfvtgivswg  egcarkgkyg  iytkvtaflk  widrsmktrg  lpkakshape 481      vitssplk (Light chain of human coagulation factor Xa)
                                                                    SEQ ID NO: 2
    1      ansfleemkk  ghlerecmee  tcsyeearev  fedsdktnef  wnkykdgdqc  etspcqnqgk 61      ckdglgeytc  tclegfegkn  celftrklcs  ldngdcdqfc  heeqnsvvcs  cargytladn 121      gkaciptgpy  pcgkqtler                                              139

(Heavy chain of human coagulation factor Xa)
                                                                    SEQ ID No 3
    1      ivggqeckdg  ecpwqallin  eenegfcggt  ilsefyilta  ahclyqakrf  kvrvgdrnte 61      qeeggeavhe  vevvikhnrf  tketydfdia  vlrlktpitf  rmnvapaclp  erdwaestlm 121      tqktgivsgf  grthekgrqs  trlkmlevpy  vdrnscklss  sfiitqnmfc  agydtkqeda 181      cqgdsggphv  trfkdtyfvt  givswgegca  rkgkygiytk  vtaflkwidr  smktrglpka 241      kshapevits  splk
```

-continued

SEQ ID NO: 4
1  tkfvppnyyyvhqnfdrvay

SEQ ID NO: 5
1  kkfvppkksqefyekfdlvsy (human coagulation FX gene; 1-1473 bp)

SEQ ID NO: 6 atggcgcacgtccgaggcttgcagctgcctggctgcctggccctggctgccctgtgtagccttgtgcacagccag
catgtgttcctggctcctcagcaagcacggtcgctgctccagcgggtccggcgagccaattcctttcttgaagag
atgaagaaaggacacctcgaaagagagtgcatggaagagacctgctcatacgaagaggcccgcgaggtctttgag
gacagcgacaagacgaatgaattctggaataaatacaaagatggcgaccagtgtgagaccagtccttgccagaac
cagggcaaatgtaaagacggcctcggggaatacacctgcacctgtttagaaggattcgaaggcaaaaactgtgaa
ttattcacacggaagctctgcagcctggacaacggggactgtgaccagttctgccacgaggaacagaactctgtg
gtgtgctcctgcgcccgcgggtacaccctggctgacaacggcaaggcctgcattccacagggccctacccctgt
gggaaacagaccctggaacgcaggaagaggtcagtggcccaggccaccagcagcagcggggaggcccctgacagc
atcacatggaagccatatgatgcagccgacctggaccccaccgagaaccccttcgacctgcttgacttcaaccag
acgcagcctgagaggggcgacaacaacctcacgcgtatcgtgggaggccaggaatgcaaggacggggagtgtccc
tggcaggccctgctcatcaatgaggaaaacgagggtttctgtggtggaactattctgagcgagttctacatccta
acggcagcccactgtctctaccaagccaagagattcaaggtgagggtaggtgaccggaacacggagcaggaggag
ggcggtgaggcggtgcacgaggtggaggtggtcatcaagcacaaccggttcacaaaggagacctatgacttcgac
atcgccgtgctccggctcaagacccccatcaccttccgcatgaacgtggcgcctgcctgcctccccgagcgtgac
tgggccgagtccacgctgatgacgcagaagacggggattgtgagcggcttcgggcgcacccacgagaagggccgg
cagtccaccaggctcaagatgctggaggtgcccctacgtggaccgcaacagctgcaagctgtccagcagcttcatc
atcacccagaacatgttctgtgccggctacgacaccaagcaggaggatgcctgccaggggggacagcgggggcccg
cacgtcacccgcttcaaggacacctacttcgtgacaggcatcgtcagctggggagagggctgtgcccgtaagggg
aagtacgggatctacaccaaggtcaccgccttcctcaagtggatcgacaggtccatgaaaaccaggggcttgccc
aaggccaagagccatgccccggaggtcataacgtcctctccattgaaa (DNA sequence of modified human FX - type A; 1-1509 bp)

SEQ ID NO: 7

Atggcgcacgtccgaggcttgcagctgcctggctgcctggccctggctgccctgtgtagccttgtgcacagccag catgtgttcctggctcctcagcaagcacggtcgctgctccagcgggtccggcgagccaattcctttcttgaagag atgaagaaaggacacctcgaaagagagtgcatggaagagacctgctcatacgaagaggcccgcgaggtctttgag gacagcgacaagacgaatgaattctggaataaatacaaagatggcgaccagtgtgagaccagtccttgccagaac cagggcaaatgtaaagacggcctcggggaatacacctgcacctgtttagaaggattcgaaggcaaaaactgtgaa .ttattcacacggaagctctgcagcctggacaacggggactgtgaccagttctgccacgaggaacagaactctgt ggtgtgctcctgcgcccgcgggtacaccctggctgacaacggcaaggcctgcattcccacagggccctacccctg tgggaaacagaccctggaacgcaggaagaggtcagtggcccaggccaccagcagcagcggggaggcccctgacag catcacatggaagccatatgatgcagccgacctggaccccaccgagaaccccttcgacctgcttgacttcaacca gacgcagcctgagaggggcgacaacaacctcacgcgtatcgtgggaggccaggaatgcaaggacggggagtgtcc ctggcaggccctgctcatcaatgaggaaaacgagggtttctgtggtggaactattctgagcgagttctacatcct aacggcagcccactgtctctaccaagccaagagattcaaggtgagggtaggtgaccggaacacggagcaggagga gggcggtgaggcggtgcacgaggtggaggtggtcatcaagcacaccaagttcgtgccccctaactactattacgt ccaccagaattttgaccgggtggcctatgacttcgacatcgccgtgctccggctcaagacccccatcaccttccg catgaacgtggcgcctgcctgcctccccgagcgtgactgggccgagtccacgctgatgacgcagaagacggggat -continued

```
tgtgagcggcttcgggcgcacccacgagaagggccggcagtccaccaggctcaagatgctggaggtgccctacgt ggaccgcaacagctgcaagctgtccagcagcttcatcatcacccagaacatgttctgtgccggctacgacaccaa gcaggaggatgcctgccaggggga cagcgggggcccgcacgtcacccgcttcaaggacacctacttcgtgacagg catcgtcagctggggagagggctgtgcccgtaaggggaagtacgggatctacaccaaggtcaccgccttcctcaa gtggatcgacaggtccatgaaaaccaggggcttgcccaaggccaagagccatgccccggaggtcataacgtcctc tccattgaaa
```

(DNA sequence of modified human FX - type B; 1-1512 bp)

SEQ ID NO: 8

```
atggcgcacgtccgaggcttgcagctgcctggctgcctggccctggctgcc (FIG. 2B) or vptFXa (FIG. 2C) in the absence (grey line/ grey column) or presence of 0.4 μM rivaroxaban ("riva," black line/black column) or 2 μM apixaban ("api," dotted line/white column). Thrombin formation was assessed using a fluorogenic substrate and peak thrombin concentrations of the various incubations are shown in the insets.

Figure 3A:
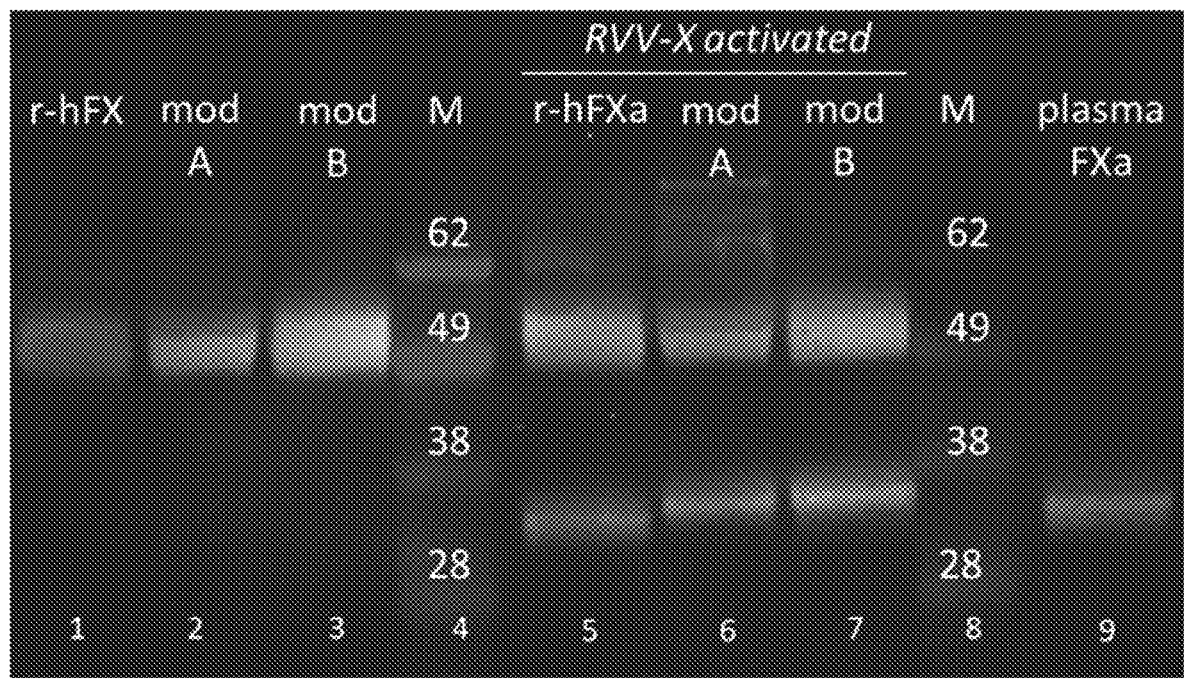
Figure 3B:
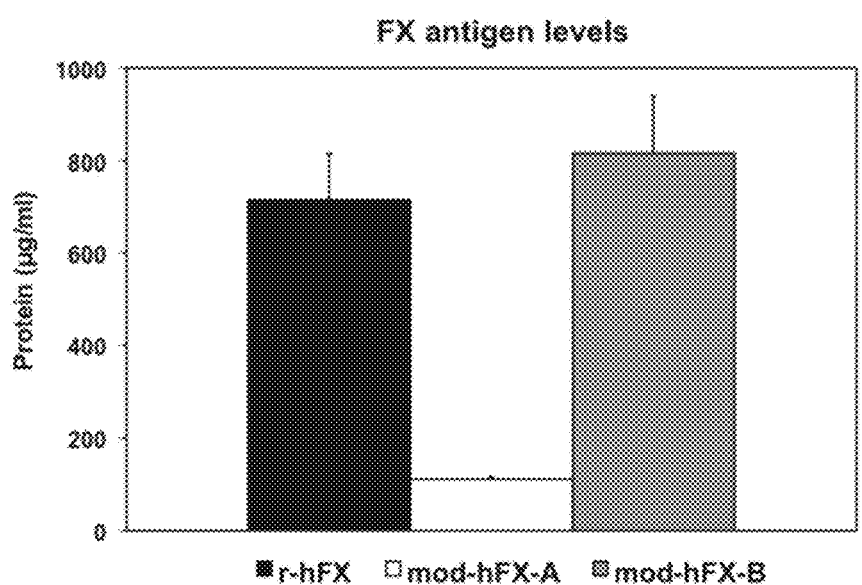

FIGS. 3A and 3B: FIG. 3A: Fluorescent Western blot of recombinant FX (200 ng) obtained from HEK293 cell lines that stably express either recombinant human FX (r-hFX, lane 1, 5), modified human FX-A (mod A, lane 2, 6) or modified human FX-B (mod B, lane 3, 7), before (lanes 1, 2, 3) or after (lanes 5, 6, 7) incubation with RVV-X activator. The heavy chain of endogenous plasma-derived human FXa migrates at ~29 kDa (lane 9). Relative weight (kDa) of the protein markers (lanes 4, 8) are indicated. FIG. 3B: Recombinant FX in conditioned media from HEK293 cell lines stably expressing either recombinant human FX (black column), modified human FX-A (white column) or modified human FX-B (grey column) was quantified using an FX-specific ELISA. Each individual bar represents a single stable cell line with the highest attainable expression per FX variant.

Figure 4:
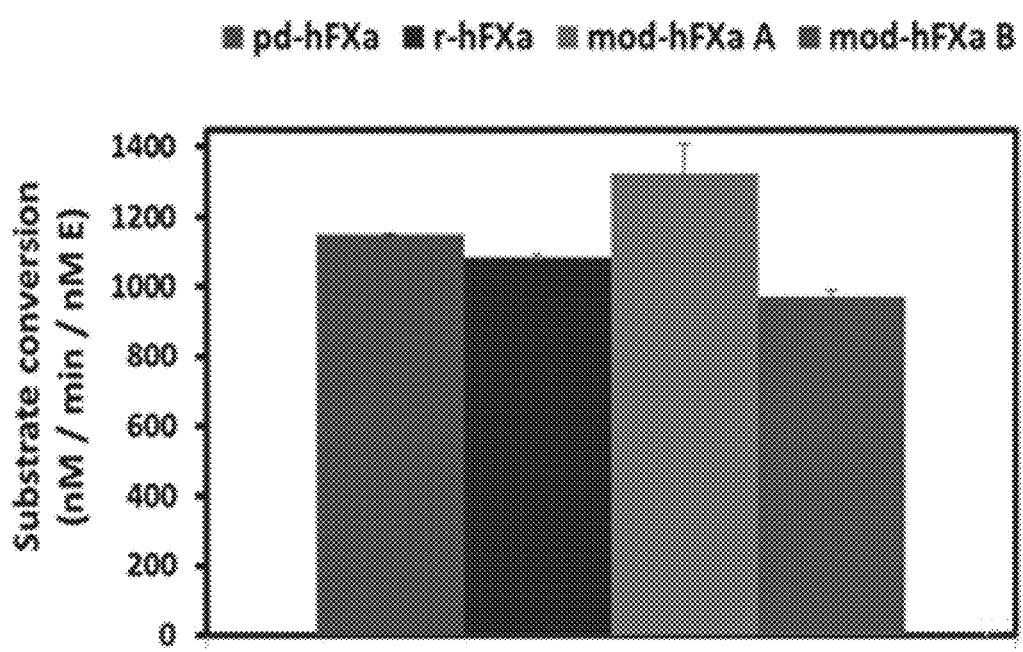

FIG. 4: Macromolecular substrate activation. Prothrombin conversion (1.4 μM) in the presence of 50 μM PCPS, 20 nM FV (FV810, recombinant B-domain truncated FV) and 0.1 nM of modified human coagulation FXa type A (m-hFXa A), type B (m-hFXa B), recombinant (r-hFXa), or plasma-derived (pd-hFXa) FXa. The substrate conversion is plotted in nM/min/nM Enzyme and data are the mean value of two independent experiments ±S.D.

Figure 5A:
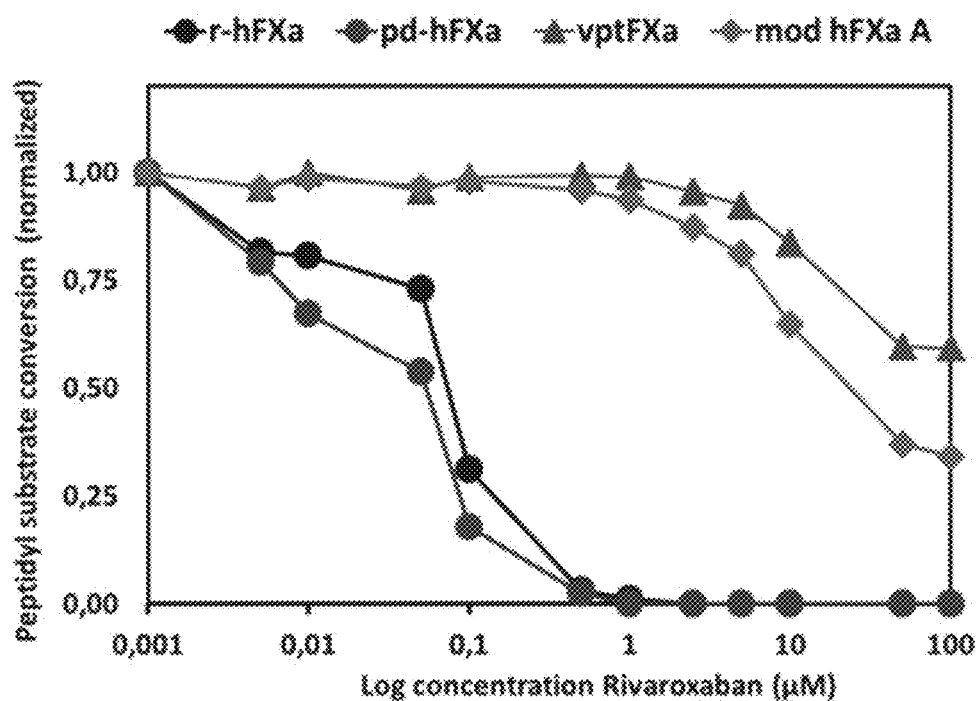
Figure 5B:
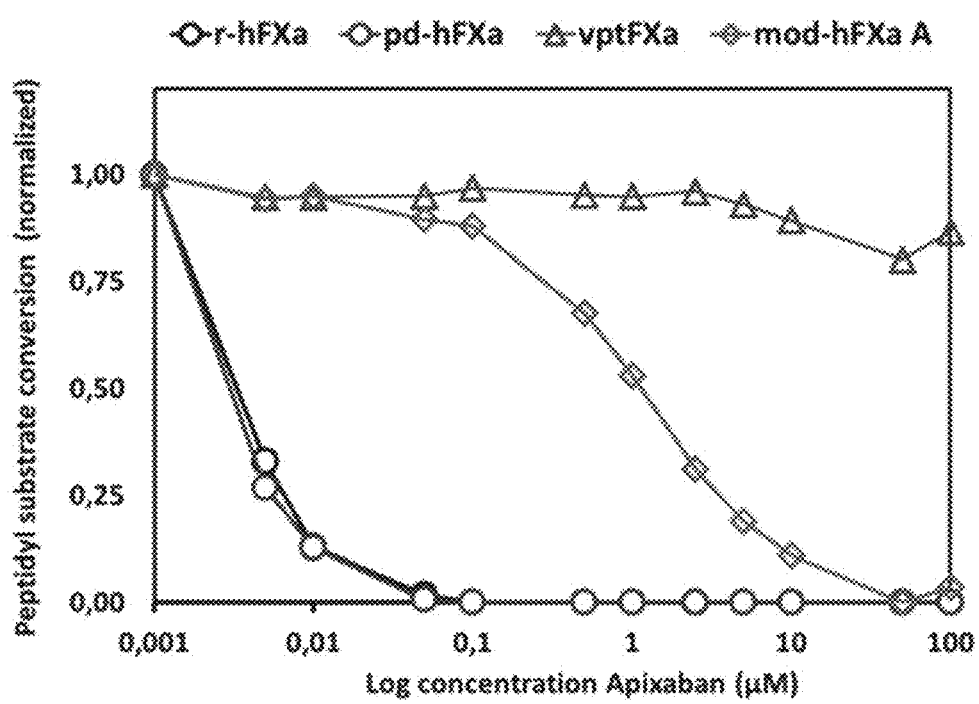

FIGS. 5A and 5B: Inhibition of FXa chimer type-A by DFXIs. Peptidyl substrate conversion (SpecFXa, 250 μM) of RVV-X activated modified human coagulation FXa type A (m-hFXa A, 1 nM) in comparison to recombinant human coagulation FXa (r-hFXa, 3 nM), plasma-derived human coagulation FXa (pd-FXa, 2 nM), and venom P. textilis (vptFXa, 1 nM) FXa. Conversion rates were determined in the presence of 0.001-100 μM of Rivaroxaban (FIG. 5A) or Apixaban (FIG. 5B). The data represent the mean value of two independent experiments, except for r-hFXa (n=1).

Figure 6A:
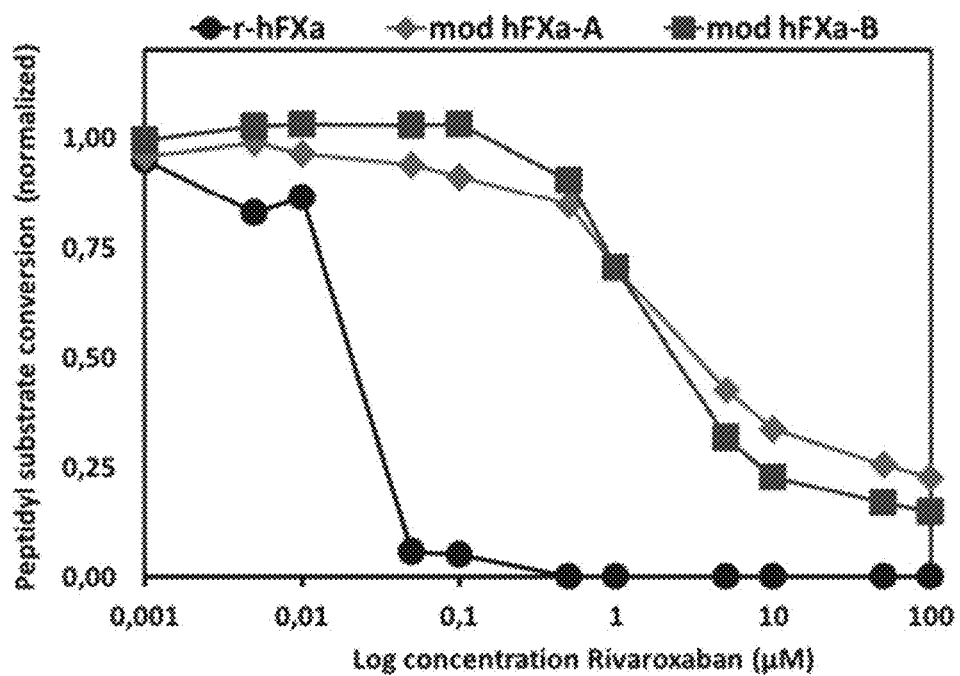
Figure 6B:
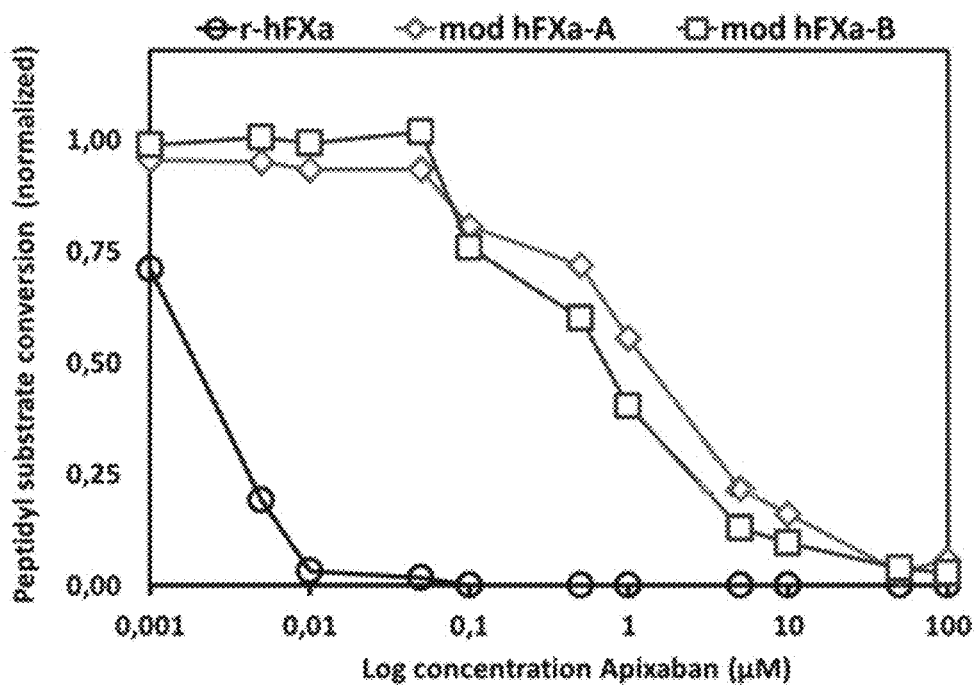

FIGS. 6A and 6B: Inhibition of modified human FX-A and modified human FX-B by DFXIs. Peptidyl substrate conversion (SpecFXa, 250 μM) by RVV-X activated modified human FX-A (m-hFXa A, 1 nM) and modified human FX-B (m-hFXa B, 7 nM, in comparison to RVV-X-activated recombinant human coagulation FXa (r-hFXa, 6 nM). Conversion rates were determined in the presence of 0.001-100 μM of rivaroxaban (FIG. 6A) and apixaban (FIG. 6B). The data are the means of two independent experiments.

Figure 7A:
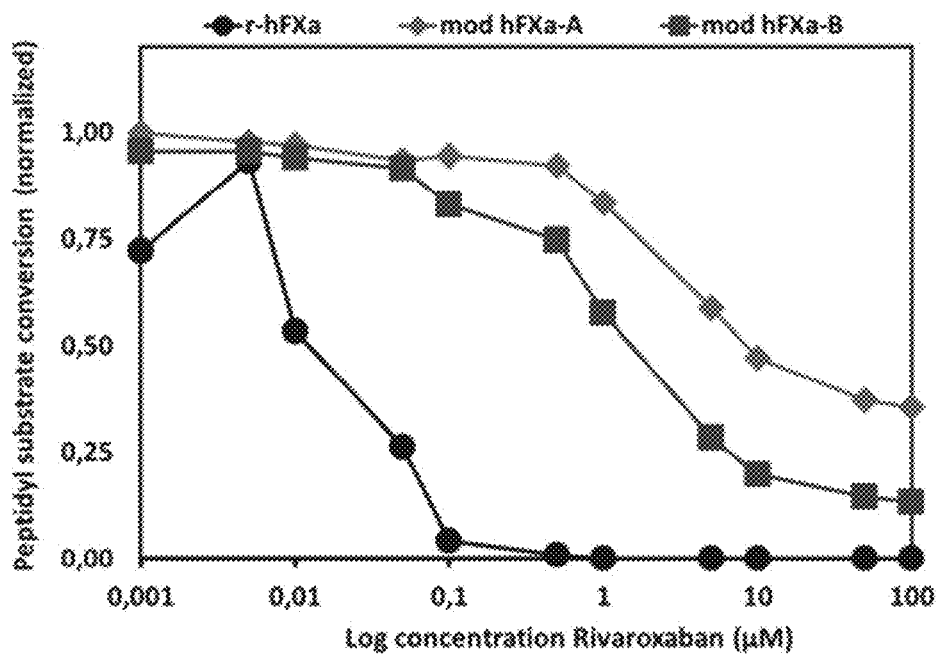
Figure 7B:
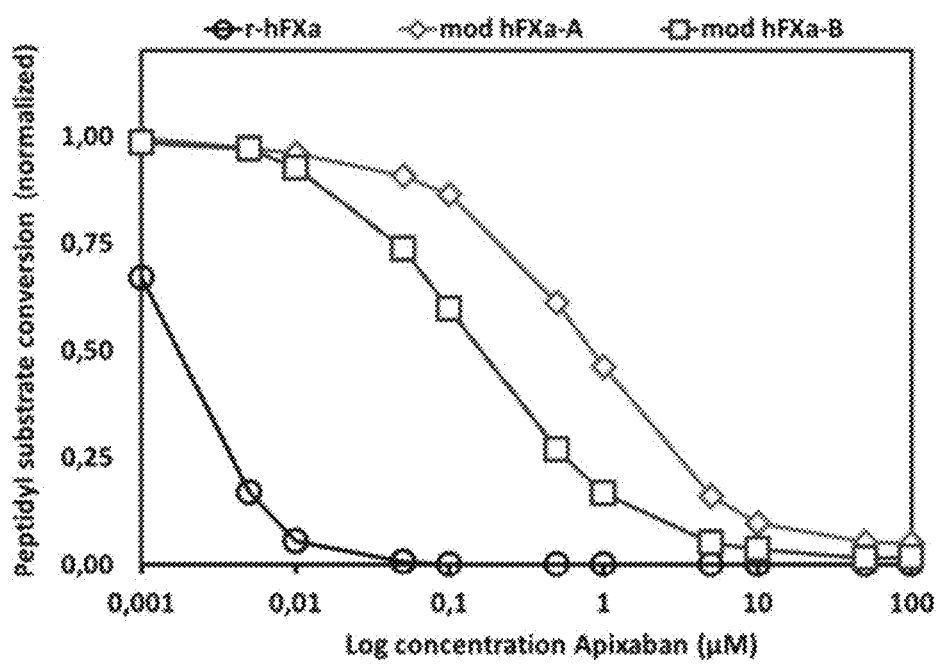

FIGS. 7A and 7B: Inhibition of modified human FX-A or modified human FX-B by DFXIs in the presence of cofactor Va and phospholipids. Peptidyl substrate conversion (SpecFXa, 250 μM) by RVV-X activated modified human FX-A (m-hFXa A, 2 nM) and activated modified human FX-B (m-hFXa B, 4 nM) in comparison to by RVV-X activated recombinant human coagulation FXa (r-hFXa, 3 nM), in the presence of 50 μM PCPS and 30 nM FV (FV810, recombinant B-domain truncated). Conversion rates were determined in the presence of 0.001-100 μM of Rivaroxaban (FIG. 7A) or Apixaban (FIG. 7B). The data are the means of two independent experiments.

FIGS. 8A-8C: Multiple alignment of coagulation FX proteins of different species. The amino acid sequence of human coagulation FX (Genbank Accession No.: AAH46125.1) (HUM) (SEQ ID NO:1) is compared to the amino acid sequences of M. musculus coagulation FX (Genbank Accession No.: AAC36345.1) (MUS) (SEQ ID NO:29), X. tropicalis coagulation FX (Genbank Accesion No.: NP 001015728) (Xtr) (SEQ ID NO:30), D. rerio coagulation FX (Genbank Accession No.: AAM88343.1) (Dre) (SEQ ID NO:31), T. rubripes coagulation FX (Genbank Accession No.: NP 001027783.1) (Tru) (SEQ ID NO:32), P. textilis coagulation FX isoform 1 (UniprotKB accession No.: Q1L659) (Pte1) (SEQ ID NO:33), P. textilis coagulation FX isoform 2 (UniprotKB accession No.: Q1L658) (Pte2) (SEQ ID NO:34), P. textilis coagulation FX (pseutarin C catalytic subunit precursor; Genbank Accession No.: AAP86642.1) (Pte3) (SEQ ID NO:35) and N. scutatus coagulation FX (UniProtKB accession No.: P82807.2) (Nsc) (SEQ ID NO:36). In these figures, Gly-289, Asp-320, Tyr-319, Glu-297, Val-305 and His-311 of SEQ ID NO:1 are indicated in bold and are underlined. These figures show that there is variation in the region of amino acid residues corresponding to the region between Gly-289 and Asp-320 of SEQ ID NO:1 between coagulation FX proteins of different species. Amino acid residues that are conserved in all species are indicated in the consensus sequence.

FIG. 9: Amino acid composition of endogenous hFX and chimeric FX variants. Serine protease domain residues Histidine91 and Tyrosine99 (chymotrypsin numbering; corresponding to His 311 and Tyrosine 319, respectively, of FX as depicted in SEQ ID NO:1) of endogenous human (hFX) in alignment with chimeric FX type A (c-FX A, middle; sequence between His 311 and Asp 320 corresponds to SEQ ID NO:9), type B (c-FX B; sequence between His 311 and Asp 320 corresponds to SEQ ID NO:10), and type C (c-FX C; sequence between His 311 and Asp 320 corresponds to SEQ ID NO:11).

Figure 10:
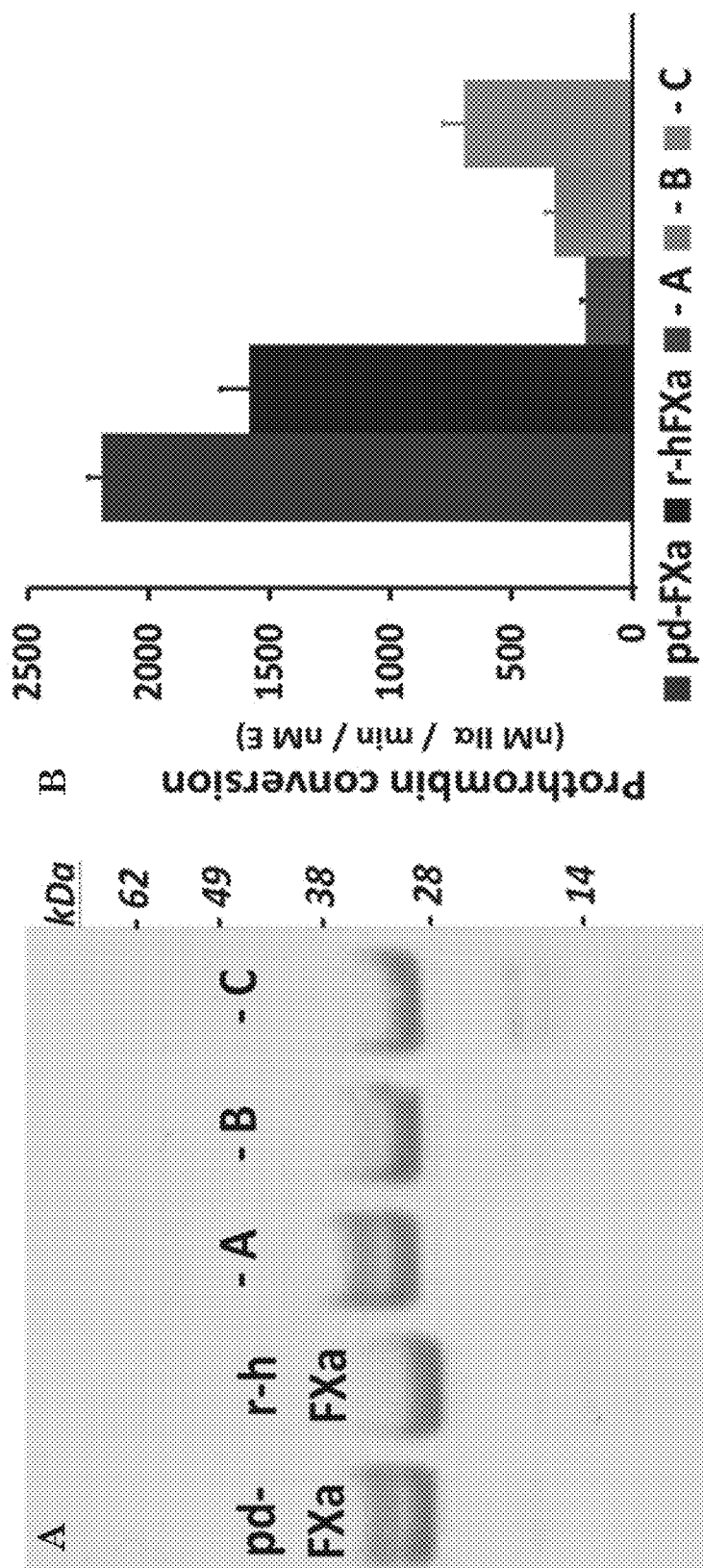

FIG. 10: Characterization of FXa: Panel A: Coomassie staining of 5 μg FXa variants on 4-12% Bis-Tris gels. From left to right: plasma-derived Factor Xa (pd-FXa), r-hFXa, chimeric factor Xa type A, B and C (-A, -B, -C). Panel B: Prothrombin conversion (1.4 μM) in the presence of 50 μM PCPS (75% phosphatidylcholine, 25% phosphatidylserine) and 20 nM FV (FV810, recombinant B-domain truncated FV) and 0.1 nM of pd-FXa, r-hFXa, c-FXa-A, c-FXa-B and c-FXa-C. Data points are the mean value of two independent experiments.

Figure 11:
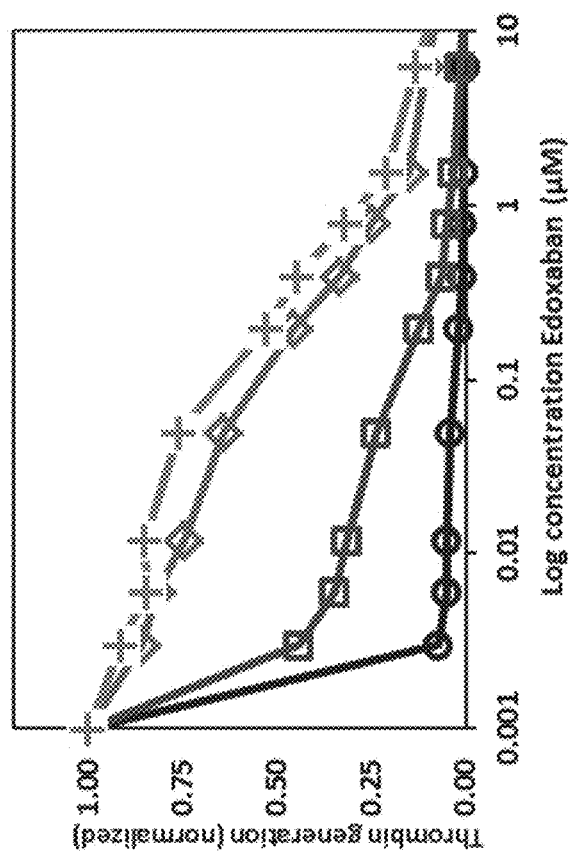
Figure 11:
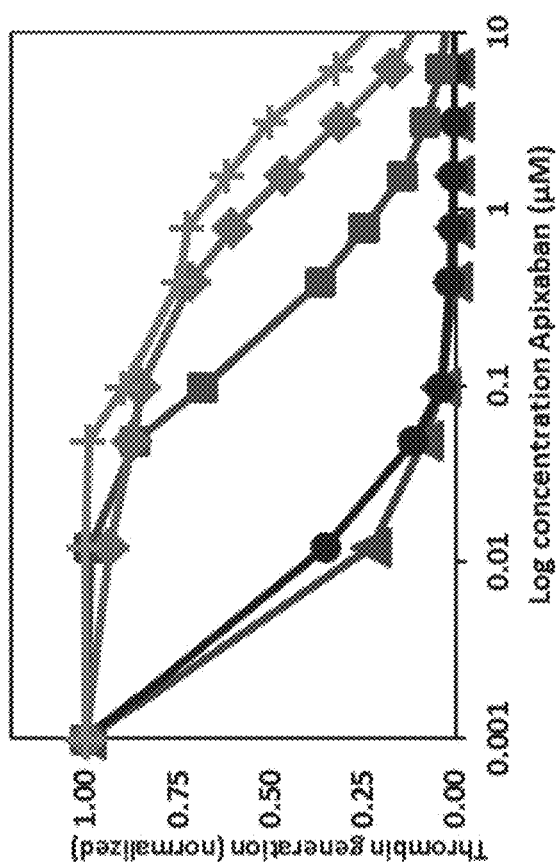

FIG. 11: Inhibition of FXa variants by DOACs. Normalized prothrombin conversion by 1 nM of pd-FXa (triangles), r-hFXa (circles), chimeric FXa-A (squares), -B (diamonds) and -C (crosses) was assessed in the presence of 0.001-100 μM of Apixaban (left, closed symbols) or Edoxaban (right, open symbols). Inhibitory constants (determined with Graphpad Prism 6 software suite) of Apixaban for pd-FXa: 2 nM, r-hFXa: 4 nM, c-FXa-A: 130 nM, -B: 760 nM-C: 1270 nM and of Edoxaban for r-hFXa: 0.5 nM, c-FXa-A: 3 nM, -B: 140 nM-C: 270 nM.

Figure 12A:
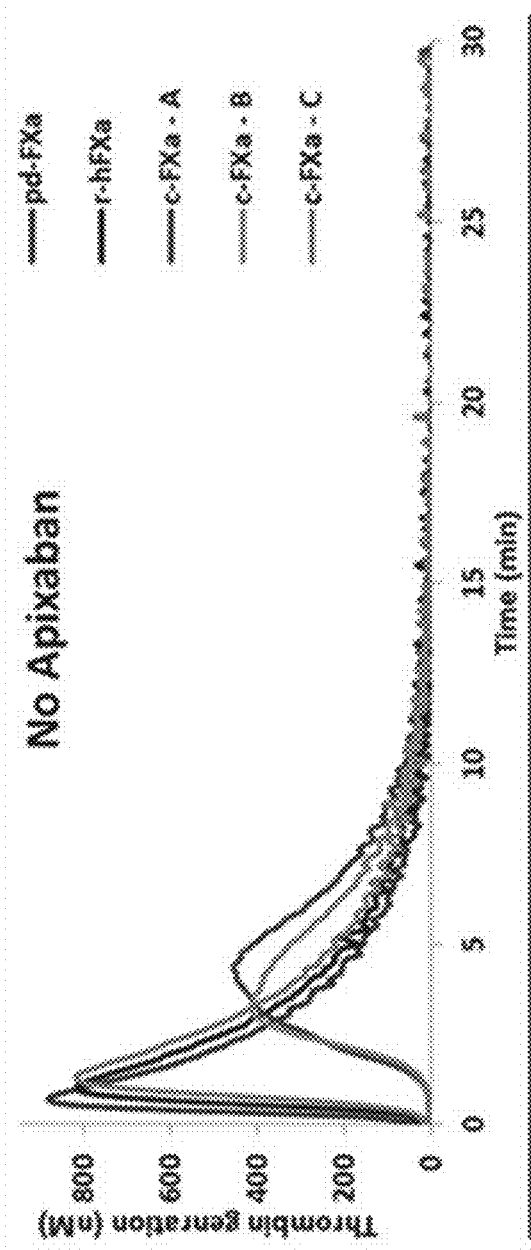
Figure 12B:
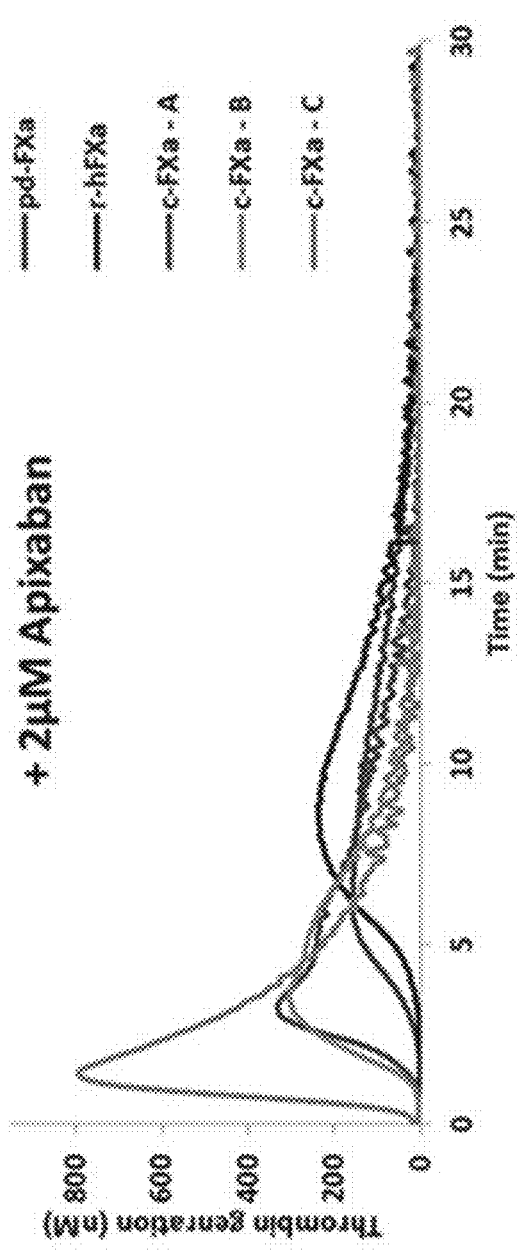

FIGS. 12A and 12B: FXa-initiated thrombin generation (TG) profiles for FXa variants. Plasma TG in the absence (FIG. 12A) and presence (FIG. 12B) of DOAC Apixaban (2 Initiation of TG by pd-FXa, r-hFXa, c-FXa-A, c-FXa-B and c-FXa-C in FX-depleted plasma. Curves are the average of at least three independent experiments.

Figure 13A:
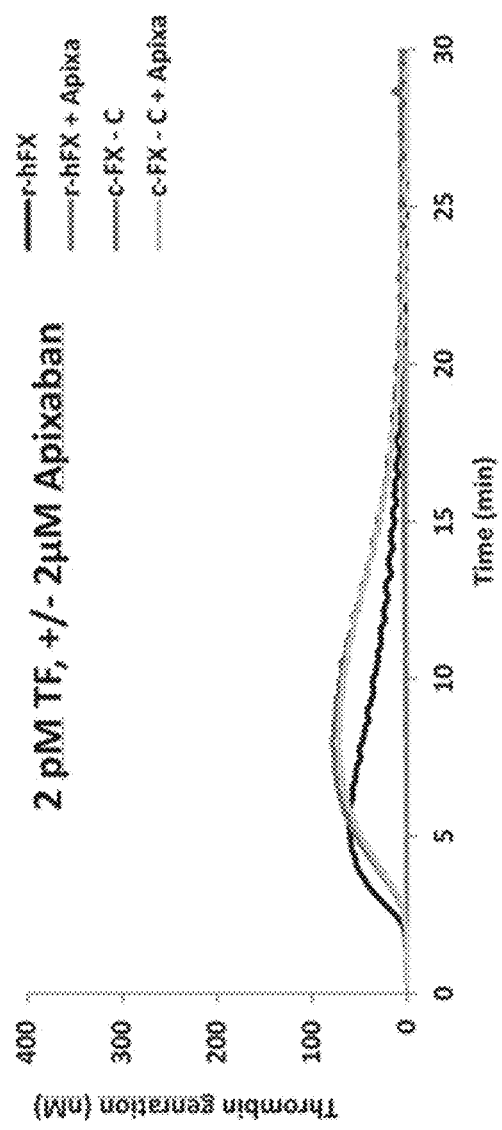
Figure 13B:
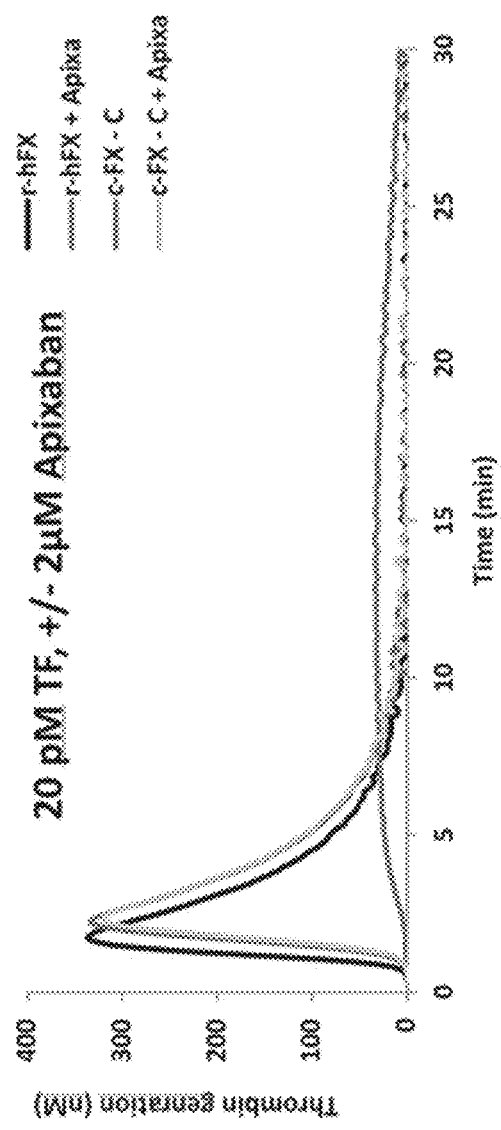

FIGS. 13A and 13B: Tissue factor (TF)-initiated TG profile for r-hFX and c-FX-C. FIG. 13A: Plasma TG at low TF (2 pM) in the absence and presence of 2 μM DOAC Apixaban (Apixa) by 1 unit r-hFX, r-hFX plus Apixaban, c-FXa-C or c-FXa-C plus Apixaban. One unit of r-hFX (7 μg/ml) or c-FXa-C (16 μg/ml) was defined by a prothrombin time-based clotting assay using normal human plasma as reference. Curves represent the average of at least three independent experiments. FIG. 13B: Plasma TG at high TF (20 pM).

Figure 14A:
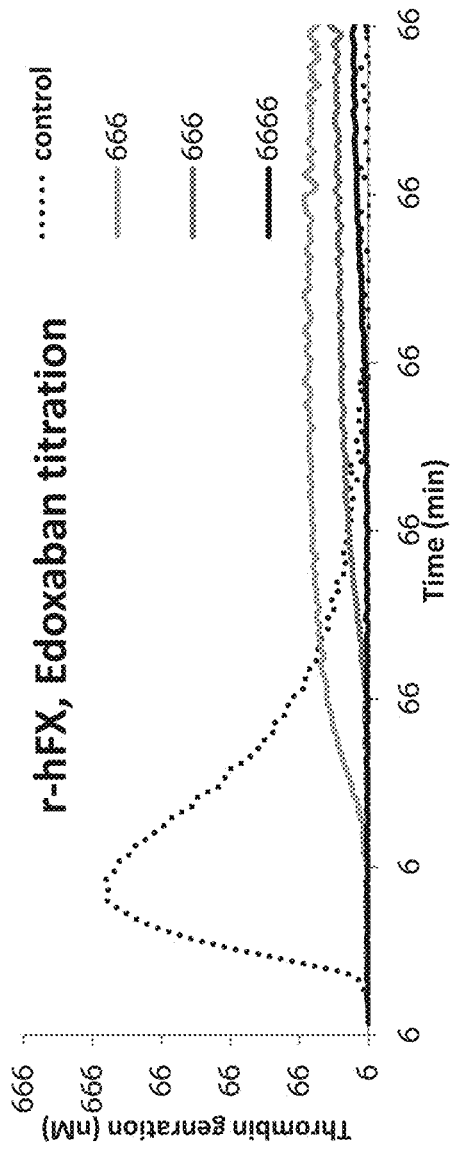
Figure 14B:
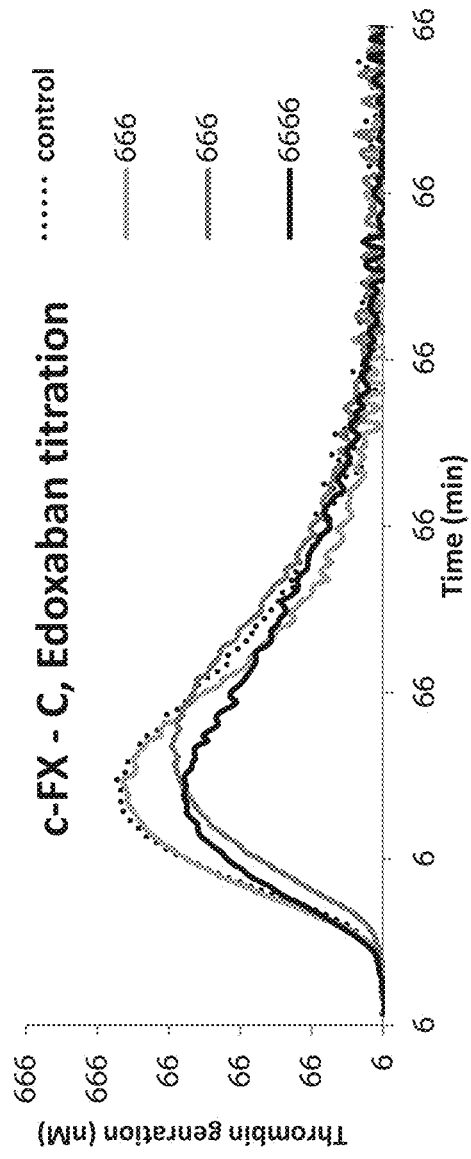

FIGS. 14A and 14B: TF-initiated TG profile for r-hFX and c-FX-C. (Upper graph): Plasma TG at low TF (2 pM) in the absence (dotted line) and presence of 200 nM (light grey), 600 nM (dark grey) and 2000 nM (black) DOAC Edoxaban by 1 unit r-hFX (7 µg/ml). (Lower graph): Plasma TG at low TF (2 pM) with similar concentrations of Edoxaban by 1 unit of c-FXa-C (16 µg/ml). Curves represent the average of two independent experiments.

TABLE 1

| Amino Acid | 3-Letter[114] | 1-Letter[114] | Side-chain polarity[114] | Side-chain charge (pH 7.4)[114] | Hydropathy Index[115] | Absorbance λmax(nm)[116] | ε at λmax (×10⁻³ M⁻¹ cm⁻¹)[116] |
|---|---|---|---|---|---|---|---|
| Alanine | Ala | A | nonpolar | neutral | 1.8 | | |
| Arginine | Arg | R | Basic polar | positive | −4.5 | | |
| Asparagine | Asn | N | polar | neutral | −3.5 | | |
| Aspartic acid | Asp | D | acidic polar | negative | −3.5 | | |
| Cysteine | Cys | C | nonpolar | neutral | 2.5 | 250 | 0.3 |
| Glutamic acid | Glu | E | acidic polar | negative | −3.5 | | |
| Glutamine | Gln | Q | polar | neutral | −3.5 | | |
| Glycine | Gly | G | nonpolar | neutral | −0.4 | | |
| Histidine | His | H | Basic polar | positive (10%) neutral (90%) | −3.2 | 211 | 5.9 |
| Isoleucine | Ile | I | nonpolar | neutral | 4.5 | | |
| Leucine | Leu | L | nonpolar | neutral | 3.8 | | |
| Lysine | Lys | K | Basic polar | positive | −3.9 | | |
| Methionine | Met | M | nonpolar | neutral | 1.9 | | |
| Phenylalanine | Phe | F | nonpolar | neutral | 2.8 | 257, 200, 188 | 0.2, 9.3, 00.0 |
| Proline | Pro | P | nonpolar | neutral | −1.6 | | |
| Serine | Ser | S | polar | neutral | −0.8 | | |
| Threonine | Thr | T | polar | neutral | −0.7 | | |
| Tryptophan | Trp | W | nonpolar | neutral | −0.9 | 280, 219 | 5.6, 47.0 |
| Tyrosine | Tyr | Y | polar | neutral | −1.3 | 274, 222, 193 | 1.4, 8.0, 48.0 |
| Valine | Val | V | nonpolar | neutral | 4.2 | | |

DETAILED DESCRIPTION

Examples

Example 1

Materials and Methods

Rivaroxaban and Apixaban were obtained from Alsachim (Illkirch, France) and dissolved in DMSO (~30 mg/ml). The peptidyl substrate methoxycarbonylcyclohexylglycylglycylarginine-p-nitroanilide (Spec-Xa) was obtained from Sekisui Diagnostics (Stamford, Conn., USA). All tissue culture reagents were from Life Technologies (Carlsbad, Calif.), except insulin-transferrin-sodium selenite (ITS), which was from Roche (Basel, Switzerland). Small unilamellar phospholipid vesicles (PCPS) composed of 75% (w/w) hen egg L-phosphatidylcholine and 25% (w/w) porcine brain L-phosphatidylserine (Avanti Polar Lipids, Alabaster, Ala.) were prepared and characterized as described previously (Higgins et al., J. Biol. Chem. 1983, 258:6503-6508). FX-depleted human plasma was obtained from Diagnostica Stago (Paris, France). All functional assays were performed in HEPES buffered Saline (20 mM Hepes, 0.15 M NaCl, pH 7.5) supplemented with 5 mM CaCl2 and 0.1% polyethylene glycol 8000 (assay buffer). Mammalian expression vector pCMV4 (Andersson et al., J. Biol. Chem. 1989, 264:8222-8229, carrying recombinant human FX (r-hFX) was a generous gift from Rodney M. Camire (Camire et al., Biochemistry 2000, 39:14322-14329). The pcDNA3 vector was obtained from Invitrogen and the PACE cDNA was a generous gift from Genetics Institute, Boston, Mass. A vector carrying Furin proprotein convertase has been described (U.S. Pat. No. 5,460,950).

Human recombinant Factor V (FV) was prepared, purified, and characterized as described previously (Bos et al., Blood 2009, 114:686-692). Recombinant P. textilis venom FXa (vpt-FXa) was prepared, purified, and characterized as described previously (Verhoef et al., Toxin Reviews (2013) (doi:10.3109/15569543.2013.844712)). Plasma-derived human Factor Xa (pd-hFXa), DAPA, human prothrombin and Anti-Human Factor X monoclonal mouse IgG (AHX-5050) were from Haematologic Technologies (Essex Junction, VT, USA). FX antigen paired antibodies for ELISA were obtained from Cedarlane (Burlington, Canada). RVV-X activator was obtained from Diagnostica Stago (Paris, France), or Haematologic Technologies. Restriction endonuclease ApaI was obtained from New England Biolabs (Ipswich, Mass., USA). T4-DNA ligase was obtained from Roche (Roche Applied Science, Indianapolis, Ind., USA).

The DNA sequence encoding modified human FX-A is provided as SEQ ID NO:7. The DNA sequence encoding modified human FX-B is provided as SEQ ID NO:8. Nucleotides encoding SEQ ID NO:4 (to generate modified human FX-A) or SEQ ID NO:5 (to generate modified human FX-B) sequences flanked by ApaI restriction sites were synthesized by Genscript (Piscataway, N.J., USA), subcloned into pCMV4 mammalian expression vector using ApaI and T4-DNA ligase and sequenced for consistency. Modified human FX-A and modified human FX-B are also referred to as mod-hFX-A and mod-hFX-B, respectively. Stable HEK293 cell lines expressing r-hFX or modified hFX were obtained as described previously (Larson et al., Biochemistry 1998, 37:5029-5038). HEK293 cells were cotransfected with pCMV4 and pcDNA-PACE vectors using Lipofectamine2000 according to the manufacturer's instructions. FX expression of transfectants was assessed by a modified one-step clotting assay using FX-depleted human plasma. Transfectants with the highest expression levels were expanded into T175 culture flasks and conditioned for 24 hours on expression media (DMEM-F12 nutrient mixture without Phenol-red supplemented with: Penicillin/Streptomycin/Fungizone, 2 mM L-glutamine, 10 µg/ml ITS, 100 µg/ml Geneticin-418 sulphate and 6 µg/ml vitamine K). Conditioned media was collected, centrifuged at 10,000 g to remove cellular debris, concentrated in a 10-kDa cut-off filter (Millipore, Darmstadt, Germany), washed with HEPES-buffered saline and stored in 50% glycerol at −20°

C. FX antigen levels of glycerol stocks were assessed by sandwich ELISA according to the manufacturer's instructions using human pooled plasma as reference, assuming a plasma FX concentration of 10 µg/ml.

Expression media was conditioned for 24 hours on stable cell lines expressing either r-hFX, modified human FX-A or modified human FX-B. An aliquot of conditioned media was incubated with RVV-X (10 ng/µl; Haematologic Technologies) for 120 minutes at 37° C. After activation, modified human FX-A or modified human FX-B are also referred to as m-hFXa A or m-hFXa B, respectively. Assuming similar substrate affinities for all FXa variants, the concentration of FXa in media was subsequently determined by peptidyl substrate conversion (Spec-Xa, 250 µM) using known concentrations of pd-hFXa as reference. Steady-state initial velocities of macromolecular substrate cleavage were determined discontinuously at 25° C. as described (Camire, J. Biol. Chem. 2002, 277:37863-70). Briefly, progress curves of prothrombin activation were obtained by incubating PCPS (50 µM), DAPA (10 µM), and prothrombin (1.4 µM) with human recombinant FV-810 (B-domain truncated, constitutively active), and the reaction was initiated with either 0.1 nM of pd-hFXa, r-hFXa, m-hFXa B, or 0.033 nM of m-hFXa A. The rate of prothrombin conversion was measured as described (Krishnaswamy et al., Biochemistry 1997, 36:3319-3330).

Recombinant FX and modified human FX-A and modified human FX-B (200 ng) were activated by RVV-X (0.5 U/ml) for 60 minutes at 37° C. and subjected to electrophoresis under reducing (30 mM dithiothreitol) conditions using pre-cast 4-12% gradient gels and the MES buffer system (Life Technologies) and transferred to a nitrocellulose membrane using the Trans-Blot Turbo Transfer System (Bio-Rad Laboratories, Hercules, Calif., USA). The blot was probed with an anti-heavy chain FX antibody and protein bands were visualized using a Dyelight-800 anti-mouse fluorescent antibody (Thermo Scientific, Rockford, Ill. USA). Plasma-derived hFXa (200 ng) was used as a reference.

Thrombin generation was adapted from protocols earlier described (Hemker et al., Pathophysiol. Haemost. Thromb. 2003, 33:4-15). Briefly, FX-depleted plasma was mixed with Corn Trypsin Inhibitor (70 µg/ml), buffer (25 mM HEPES, 175 mM NaCl, 5 mg/ml BSA, pH 7.5) and PCPS (20 µM) and incubated for 10 minutes at 37° C. in a 96-well microplate. Thrombin formation was initiated by addition of pd-hFXa (0.5 nM) or vpt-FXa (0.5 nM) preincubated with Rivaroxaban (0.4 µM) or Apixaban (0.2 supplemented with FluCa and immediately transferred to the plasma mix. The final reaction volume was 120 µl of which 64 µl was FX-depleted plasma. Thrombin formation was determined every 20 seconds for 30 minutes and corrected for the calibrator using a software suite (Thrombinoscope, version 5.0). The mean endogenous thrombin potential (the area under the thrombin generation curve) was calculated from at least two individual experiments. Calibrator and fluorescent substrate (FluCa) were purchased from Thrombinoscope (Maastricht, The Netherlands).

Peptidyl substrate conversion (Spec-Xa, 250 µM final) of each FXa variant was performed in the absence or presence of direct FXa inhibitors Rivaroxaban and Apixaban (0.001 µM-100 µM final) at ambient temperature. Calcium-free stocks of pd-hFXa (2 nM final) or vpt-FXa (10 nM final) were diluted in assay buffer and incubated in a 96-well microplate in the presence of assay buffer or inhibitor for 2 minutes. Substrate conversion was initiated with Spec-Xa and absorption was monitored for 10 minutes at 405 nM in a SpectraMax M2e microplate reader equipped with the Softmax Pro software suite (Molecular Devices, Sunnyvale, Calif., USA). In order to assay DFXI sensitivity of each recombinant FX variant, glycerol stocks (5-40 µl) of r-hFX, modified human FX-A and modified human FX-B were diluted in assay buffer and incubated with RVV-X (0.5 U/ml) for 60 minutes at 37° C. Activated stocks were subsequently diluted in assay-buffer, incubated for 2 minutes in a 96-well microplate in the presence of assay buffer or inhibitor and assayed for substrate conversion as described. The relative concentration of rhFX, m-hFXa A and m-hFXa B was assessed from the rate of substrate conversion in the absence of inhibitor using known concentrations of pd-hFXa as reference.

Results

Venom-Derived P. Textilis (Vpt)-FXa is Resistant to Inhibition by DFXIs

Figure 2A:
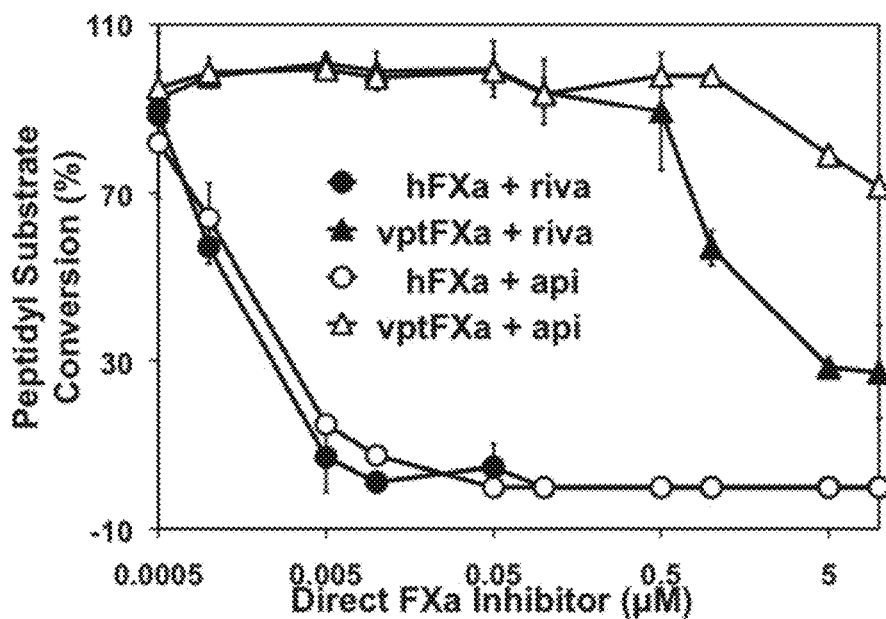
Figure 2B:
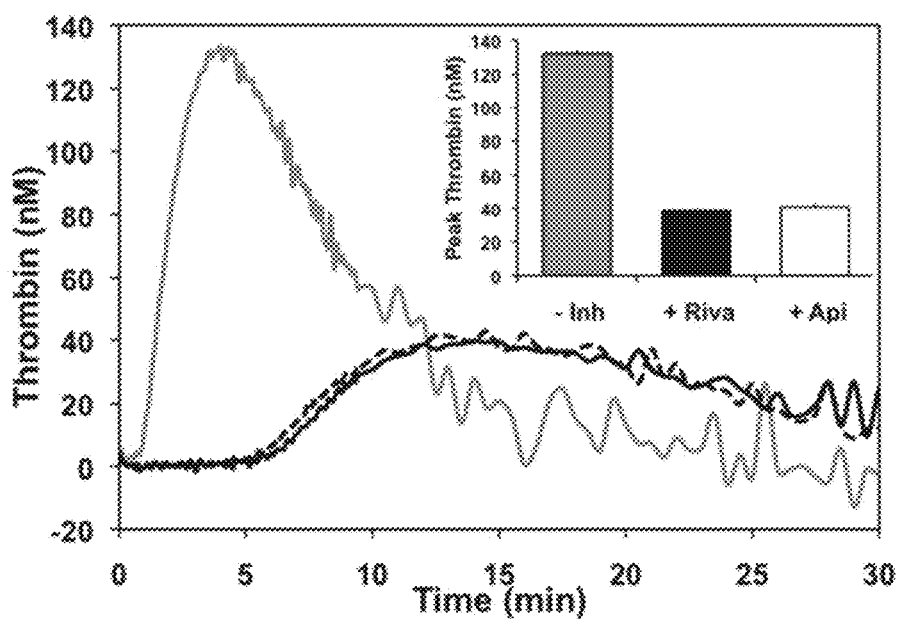
Figure 2C:
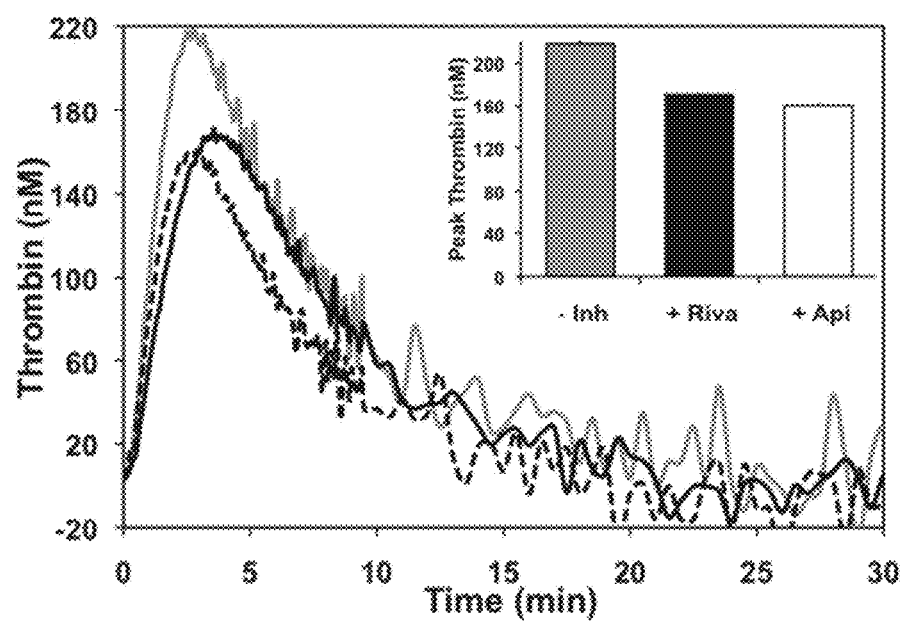

Biochemical characterization of purified recombinant venom-derived P. textilis FXa (vptFXa) revealed that this protease, unlike any other FXa species known to date, is resistant to inhibition by the direct anticoagulants rivaroxaban and apixaban, which have been designed to reversibly block the active site of FXa. Consistent with previous observations, the Ki for human FXa (hFXa) inhibition was approximately 1 nM (Perzborn, J. Thromb. Haemost. 2005, 3:514-521), whereas vptFXa inhibition was at least a 1000-fold reduced (FIG. 2A). These findings were corroborated in a plasma system mimicking in vivo fibrin generation, demonstrating that physiological concentrations of the FXa inhibitors hardly affected vptFXa-initiated thrombin formation, while a significant reduction was observed with hFXa present (FIGS. 2B and 2C).

Human-Venom P. Textilis FXa Chimeras

A striking structural element that is not only limited to vptFXa, but also present in venom FX from the Australian snake Notechis scutatus, is an altered amino acid composition at a position close to the hFXa active site (FIG. 1, Panel C). Given its location, it was hypothesized that this unique helix may not only modulate the interaction with rivaroxaban and/or apixaban, but also with FVa, as the FVa binding site is C-terminal to this helix (Lee et al., J. Thromb. Haemost. 2011, 9:2123-2126). To test this hypothesis, the two-protein coding DNA constructs as listed in SEQ ID NOS:7 and 8 were prepared. The mod-hFX-A chimera as provided in SEQ ID NO:7 comprises the relevant part of the N. scutatus DNA sequence (indicated in bold and underlined) and the mod-hFX-B chimera as provided in SEQ ID NO:8 comprises the relevant part of the P. textilis sequence (indicated in bold and underlined).

Using these DNA constructs, HEK293 cell lines were generated that stably produced both chimeric proteins and subsequently assessed the expression levels of modified human FX from HEK293 cells by conditioning the cells on expression media for 24 hours. Western blot analysis revealed expression of full-length FX for both chimeric variants similar to wild-type FX (FIG. 3A). Incubation with activator from Russell's Viper Venom (RVV-X) resulted in proteolytic activation of approximately 30% of zymogen FX to FXa, indicated by the appearance of the ~29 kDa heavy chain band. The heavy chain of both modified human FXa-A and modified human FXa-B migrated at a slightly higher molecular weight, which is consistent with the insertion of a snake sequence that is 12 or 13 residues longer as compared to that of human FXa, respectively. Analysis of the FX antigen levels in conditioned media indicated that whereas the expression of mod-hFX-A was approximately seven-fold reduced, that of mod-hFX-B was similar to wild-type human FX (FIG. 3B). The low FX antigen levels of mod-hFX-A correlated with the similarly low FX activity levels observed employing a modified clotting assay. This indicates that while the protein expression of mod-hFX-A is suboptimal as compared to that of the other FX variants, its FX function is not perturbed.

To test zymogen activation of FX, rFX and modified human FX-A and modified human FX-B was converted to FXa using FX activator from Russell's Viper Venom (RVV-X). Both modified human FXa-A and modified human FXa-B displayed protease activity upon RVV-X activation, as assessed by conversion of the small FXa-specific peptidyl substrate SpectroZyme Xa. In addition, the prothrombin conversion rates in the presence of the human cofactor FVa of both chimeras were similar to human FXa (both pd-hFXa and r-hFXa) (FIG. 4). Collectively, these observations suggest that the snake sequence insertions do not severely hamper the enzymatic properties of human FX.

Inhibition of FXa Chimeras by DFXIs

To estimate the inhibitory constant (Ki) of Rivaroxaban and Apixaban for RVV-X activated modified human FX-A, the activated recombinant protein was pre-incubated with 0.001 to 100 μM of inhibitor and subsequently assayed for its catalytic activity toward SpectroZyme Xa. While incubation with 0.5 μM Rivaroxaban resulted in full inhibition of r-hFXa and pd-hFXa, mod-hFXa-A remained fully active under these conditions (FIG. 5A). Moreover, the chimeric variant still displayed partial chromogenic activity following incubation with 100 μM Rivaroxaban, similar to the *P. textilis* venom FXa. These data indicate that the Ki for inhibition of mod-hFXa-A is at least 100-fold increased as compared to that of human FXa. A similar reduced sensitivity for inhibition by Apixaban was observed (FIG. 5B).

Assessment of the inhibition of mod-hFXa-B by rivaroxaban and apixaban resulted in a Ki similar to that observed for mod-hFXa-A (FIGS. 6A and 6B). Thus, a reduced sensitivity for inhibition by apixaban and rivaroxaban was shown. Finally, DFXI-inhibition of the chimeric FXa variants was not altered in the presence of the cofactor FVa and negatively charged phospholipid vesicles, suggesting that both the free protease as well as that assembled into an FVa-FXa-lipid-bound complex are equally resistant to inhibition by Rivaroxaban and Apixaban (FIGS. 7A and 7B).

Example 2

Materials and Methods

Unless indicated otherwise, materials and methods as used in this example were the same or similar to the materials and methods indicated in Example 1.

Construction and expression of recombinant FX: DNA encoding chimeric FX-A (c-FX A), chimeric FX-B (c-FX B) and chimeric FX-C (c-FX C) were synthesized at Genscript (Piscataway, N.J., USA), subcloned into pCMV4 mammalian expression vector using Apa1 and T4-DNA ligase and sequenced for consistency. Stabile HEK293 cell lines expressing recombinant human or recombinant chimeric FX were obtained as described previously (Larson et al., *Biochemistry* 1998, 37:5029-5038). HEK293 cells were cotransfected with pCMV4 and pcDNA-PACE vectors by LIPOFECTAMINE® 2000 according to the manufacturer's instructions.

Purification of chimeric FX(a): Recombinant chimerix FX products A, B and C were prepared, purified and characterized as described previously (Camire et al., 2000), with the exception that the immunoaffinity purification was replaced by a calcium gradient purification of FX on a POROS HQ20-sepharose column. The typical yield of fully γ-carboxylated recombinant FX was 0.9 mg/liter conditioned medium. Purified recombinant chimeric FX was activated with RVV-X (0.1 U/mg FX), isolated by size-exclusion chromatography on a Sephacryl 5200 HR column (Vt 460 ml) and stored at −20° C. in HBS containing 50% vol/vol glycerol. Purified products were visualized by Coomassie staining.

Macromolecular substrate activation: Steady-state initial velocities of macromolecular substrate cleavage were determined discontinuously at 25° C. as described (Camire, 2002). Briefly, progress curves of prothrombin activation were obtained by incubating PCPS (50 μM), DAPA (10 and prothrombin (1.4 μM) with human recombinant FV-810 (20 nM, B-domain truncated, constitutively active FV), and the reaction was initiated with either 0.1 nM of pd-hFXa, r-hFXa, c-FXa A, c-FXa B or c-FXa C. The rate of prothrombin conversion was measured as described (Krishnaswamy et al., 1997). Prothrombin conversion was assayed in absence or presence of direct FXa inhibitors Edoxaban (CAS Registry Number 912273-65-5; manufactured by Daiichi Sankyo, marketed as Savaysa) and Apixaban (0.001 μM-100 final) in order to determine DOAC sensitivity of each recombinant FXa variant.

Thrombin generation assays: Thrombin generation was adapted from protocols earlier described (Hemker et al., 2003). Briefly, thrombin generation curves were obtained by supplementing FX-depleted plasma with Tissue Factor (TF, 2 or 20 pM final), Corn Trypsin Inhibitor (70 μg/ml), PCPS (20 μM) and 1 Unit (prothrombin time-specific clotting activity) of r-hFX (7 μg/ml) or chimeric FX-C (16 μg/ml). Thrombin formation was initiated by adding Substrate buffer (Fluca) to the plasma. FXa thrombin generation curves were obtained by supplementing FX-depleted plasma with Corn Trypsin Inhibitor (70 μg/ml), assay buffer and PCPS (20 μM). Thrombin formation was initiated by addition of FXa premixed with Rivaroxaban or Apixaban, assay buffer without calcium and supplemented with Fluca. The final reaction volume was 120 μl, of which 64 μl was FX-depleted plasma. Thrombin formation was determined every 20 seconds for 30 minutes and corrected for the calibrator, using the software of Thrombinoscope. The lag time, mean endogenous thrombin potential (the area under the thrombin generation curve), time to peak and peak thrombin generation, was calculated from at least three individual experiments.

Results

The 9-13 residue insertion in the serine protease domains of *P. textilis* venom, *P. textilis* isoform and *N. scutatis* venom FXa has prompted construction of chimeras of human and snake FX. Three protein coding DNA constructs were made that incorporate each of these insertions in human FXa (FIG. 9). Using these DNA constructs, HEK293 cell lines were generated that stably produce either recombinant normal human FX (r-hFX) or three types of chimeric FX (c-FX A, c-FX B and c-FX C). Expression levels of recombinant human and chimeric FX from HEK293 cells were determined by culturing the cells on expression media for 24 hours after which the clotting activity of conditioned medium was assessed by a modified one-step PT clotting assay in FX-depleted plasma. Recombinant γ-carboxylated FX was purified from conditioned media by successive ion-exchange chromatography steps. A fraction of the FX pool was subsequently activated with the FX activator from Russell's Viper venom, isolated by size-exclusion chromatography and characterized by SDS-PAGE. The heavy chain of purified plasma-derived factor Xa migrates as a 50/50 mixture of FXa-α and FXa-β at ~34-31 kDa. While autoproteolytic excision of the C-terminal portion of FXa-α

(residues 436-447) yields the β form of FXa, both isoforms are functionally similar with respect to prothrombinase assembly, prothrombin activation, antithrombin recognition, and peptidyl substrate conversion (Pryzdial and Kessler, 1996).

The purified products of r-hFXa and chimeric FXa-B and -C migrated predominantly as FXa-β, chimeric FXa-A migrates as a 50/50 mixture of α and β FXa instead (FIG. 10, Panel A). Kinectis of macromolecular substrate activation by r-hFXa and chimeric FXa (A/B/C) on negatively charged phospholipid vesicles (PCPS) in the presence of the cofactor FVa shows that all chimeric variants assemble into the prothrombinase complex. However, the catalytic rate of chimeric FXa variants-A, -B and -C is respectively 8.2-, 6.8-, and 2.3-fold reduced compared to recombinant human FXa. Furthermore, recombinantly prepared human FXa shows a modest decrease in catalytic efficiency compared to plasma-derived FXa (FIG. 10, Panel B).

To determine the inhibitory constant (Ki) of DOACs (Apixaban, Edoxaban) for chimeric FXa (A/B/C), the kinetics of prothrombin activation in the presence of 0.001 to 100 μM of DOAC was assayed. While plasma-derived FXa and recombinant human FXa are fully inhibited at near equimolar concentrations of DOAC, all chimeric FXa variants were able to sustain prothrombin conversion at significantly higher FXa-inhibitor concentrations (Ki Apixaban:130-1270 nM, Ki Edoxaban: 3-270 nM) (FIG. 11). Given that the chimeric FXa variants comprise similarly positioned insertions with a varying length and composition of amino acids, the close proximity of these insertions to the DOAC-coordinating residue Tyr99 and/or the active site was speculated to be of direct consequence to the decreased sensitivity for the DOACs.

In order to assess the potential of chimeric FXa to restore thrombin generation in DOAC-spiked plasma, a thrombin generation (TG) assay was performed. FXa-initiated (5 nM) thrombin generation in FX-depleted human plasma demonstrated a normal TG profile for c-FXa variant C, and near normal profiles for c-FXa variants A and B (FIG. 12A). While Apixaban (2 μM) dramatically prolonged the lag time and reduced peak thrombin generation in pd-FXa- and r-hFXa-initiated TG, these parameters were unperturbed with the chimeric FXa variants present (FIG. 12B) (Table 2). These results show that chimeric FXa variants are able to restore hemostasis in DOAC-inhibited plasma. In addition, the zymogen form of chimeric FX-C is also able to sustain thrombin generation in FX-depleted plasma. Initiation of coagulation by a low Tissue Factor (TF, 2 pM) concentration generates a robust TG curve for chimeric FX-C that is not affected by Apixaban, unlike TG by r-hFX (FIG. 13A). At low TF concentration, chimeric FX-C displays a short delay in the onset of TG and time to peak; in addition, chimeric FX-C has a larger endogenous thrombin potential (ETP) and higher peak thrombin generation (Table 3). However, these values normalize at high TF (20 pM) concentrations (FIG. 13B) (Table 3). Based on the observations made in the FXa-initiated TG assay, it is expected that zymogen forms of chimeric FX variants A and B also sustain TF-initiated TG in DOAC-spiked plasma. FIGS. 14A and 14B, in combination with Table 4, provide further evidence the effect of chimeric FXa variants on restoring hemostasis in DOAC-inhibited plasma. Taken together, these results show that chimeric FX(a) is able to restore hemostasis in DOAC-inhibited plasma, both in zymogen and protease form.

TABLE 2

Effect of Apixaban on FXa-initiated TG parameters. Values represent experimental TG values obtained in the presence of Apixaban corrected for TG values obtained in the absence of Apixaban.

| | pd-FXa | r-hFXa | c-FXa -A | c-FXa -B | c-FXa -C |
|---|---|---|---|---|---|
| Lagtime arrest (seconds) | 299 | 293 | 61 | 12 | 3 |
| Delay in time to peak (seconds) | 515 | 467 | 120 | 30 | 7 |
| Peak Thrombin Generation (% of no Apixaban) | 26 | 33 | 78 | 85 | 99 |
| Area under the curve (% of no Apixaban) | 67 | 76 | 89 | 92 | 101 |

TABLE 3

Summary of low and high TF-initiated TG experiments.

| Low TF (2 pM) | r-hFX | r-hFX + Apixaban | c-FX -C | c-FX -C + Apixaban | High TF (20 pM) | r-hFX | r-hFX + Apixaban | c-FX -C | c-FX -C + Apixaban |
|---|---|---|---|---|---|---|---|---|---|
| Lagtime (seconds) | 132 ± 5 | 696 ± 162 | 185 ± 12 | 186 ± 6 | Lagtime (seconds) | 48 ± 1 | 138 ± 12 | 72 ± 2 | 78 ± 2 |
| Time to peak (seconds) | 324 ± 6 | no peak | 480 ± 24 | 492 ± 23 | Time to peak (seconds) | 114 ± 6 | 804 ± 36 | 138 ± 6 | 144 ± 9 |
| Peak thrombin (nM) | 61 ± 4 | 8 ± 4 | 78 ± 1 | 72 ± 4 | Peak thrombin (nM) | 338 ± 8 | 32 ± 4 | 334 ± 15 | 321 ± 15 |
| ETP (nM) | 567 ± 61 | no ETP | 830 ± 131 | 756 ± 38 | ETP (nM) | 973 ± 18 | 694 ± 67 | 1027 ± 19 | 1012 ± 33 |

TABLE 4

Effect of Edoxaban on TF-initiated TG parameters for r-hFX and c-FX-C. Values represent experimental TG values obtained in the presence of increasing concentrations of Edoxaban.

| Edoxaban (nM) | control | 50 | 100 | 200 | 400 | 600 | 1000 | 2000 |
|---|---|---|---|---|---|---|---|---|
| r-hFX | | | | | | | | |
| Lagtime(s) | 115 | 247 | 297 | 397 | 538 | 679 | 874 | 1180 |
| ETP remaining | 100.% | 99.3 | 87.1 | no ETP | no ETP | no ETP | no ETP | no ETP |

TABLE 4-continued Effect of Edoxaban on TF-initiated TG parameters for r-hFX and c-FX-C. Values represent experimental TG values obtained in the presence of increasing concentrations of Edoxaban.

| Edoxaban (nM) | control | 50 | 100 | 200 | 400 | 600 | 1000 | 2000 |
|---|---|---|---|---|---|---|---|---|
| Peak height % | 100.% | 41.2 | 30.8 | 23.1 | 15.9 | 13.0 | 10.1 | 7.1 |
| Time to peak(s) | 265 | 618 | 756 | 1290 | 1890 | 1932 | 2472 | 2562 |
| c-FX -C | | | | | | | | |
| Lagtime(s) | 188 | 161 | 161 | 172 | 182 | 197 | 212 | 232 |
| ETP remaining | 100.% | 87.9 | 92.5 | 88.3 | 92.7 | 96.8 | 92.7 | 82.0 |
| Peak height % | 100.% | 109.3 | 112.3 | 101.0 | 94.6 | 88.7 | 77.5 | 65.3 |
| Time to peak(s) | 433 | 382 | 388 | 418 | 448 | 483 | 538 | 578 |

SEQUENCE LISTING

<160> NUMBER OF SEQ ID NOS: 37

<210> SEQ ID NO 1
<211> LENGTH: 488
<212> TYPE: PRT
<213> ORGANISM: Homo sapiens

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu

```
                   260                 265                 270
Thr Ala Ala His Cys Leu Tyr Gln Ala Lys Arg Phe Lys Val Arg Val
            275                 280                 285

Gly Asp Arg Asn Thr Glu Gln Glu Gly Gly Glu Ala Val His Glu
        290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
            325                 330                 335

Asn Val Ala Pro Ala Cys Leu Pro Glu Arg Asp Trp Ala Glu Ser Thr
        340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
        420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
            485

<210> SEQ ID NO 2
<211> LENGTH: 139
<212> TYPE: PRT
<213> ORGANISM: Homo sapiens

<400> SEQUENCE: 2

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg
    130                 135
```

```
<210> SEQ ID NO 3
<211> LENGTH: 254
<212> TYPE: PRT
<213> ORGANISM: Homo sapiens

<400> SEQUENCE: 3

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 4
<211> LENGTH: 20
<212> TYPE: PRT
<213> ORGANISM: Artificial Sequence
<220> FEATURE:
<223> OTHER INFORMATION: fragment of altered FX

<400> SEQUENCE: 4

Thr Lys Phe Val Pro Pro Asn Tyr Tyr Val His Gln Asn Phe Asp
1               5                   10                  15

Arg Val Ala Tyr
            20

<210> SEQ ID NO 5
<211> LENGTH: 21
<212> TYPE: PRT
<213> ORGANISM: Artificial Sequence
<220> FEATURE:
<223> OTHER INFORMATION: fragment of altered FX
```

<400> SEQUENCE: 5

Lys Lys Phe Val Pro Pro Lys Lys Ser Gln Glu Phe Tyr Glu Lys Phe
1               5                   10                  15

Asp Leu Val Ser Tyr
            20

<210> SEQ ID NO 6
<211> LENGTH: 1473
<212> TYPE: DNA
<213> ORGANISM: Homo sapiens

<400> SEQUENCE: 6

```
atggcgcacg tccgaggctt gcagctgcct ggctgcctgg ccctggctgc cctgtgtagc      60
cttgtgcaca gccagcatgt gttcctggct cctcagcaag acggtcgct gctccagcgg     120
gtccggcgag ccaattcctt tcttgaagag atgaagaaag acacctcga agagagtgc      180
atggaagaga cctgctcata cgaagaggcc cgcgaggtct ttgaggacag cgacaagacg     240
aatgaattct ggaataaata caaagatggc gaccagtgtg agaccagtcc ttgccagaac     300
cagggcaaat gtaaagacgg cctcggggaa tacacctgca cctgtttaga aggattcgaa     360
ggcaaaaact gtgaattatt cacacggaag ctctgcagcc tggacaacgg ggactgtgac     420
cagttctgcc acgaggaaca gaactctgtg gtgtgctcct cgcccgcgg gtacaccctg     480
gctgacaacg gcaaggcctg cattcccaca gggccctacc cctgtgggaa acagaccctg     540
gaacgcagga gaggtcagt ggcccaggcc accagcagca gcggggaggc ccctgacagc     600
atcacatgga agccatatga tgcagccgac ctggacccca ccgagaaccc cttcgacctg     660
cttgacttca accagacgca gcctgagagg ggcgacaaca acctcacgcg tatcgtggga     720
ggccaggaat gcaaggacgg ggagtgtccc tggcaggccc tgctcatcaa tgaggaaaac     780
gagggtttct gtggtggaac tattctgagc gagttctaca tcctaacggc agcccactgt     840
ctctaccaag ccaagagatt caaggtgagg gtaggtgacc ggaacacgga gcaggaggag     900
ggcggtgagg cggtgcacga ggtggaggtg gtcatcaagc acaaccggtt cacaaaggag     960
acctatgact tcgacatcgc cgtgctccgg ctcaagaccc ccatcacctt ccgcatgaac    1020
gtggcgcctg cctgcctccc cgagcgtgac tgggccgagt ccacgctgat gacgcagaag    1080
acggggattg tgagcggctt cgggcgcacc cacgagaagg gccggcagtc caccaggctc    1140
aagatgctgg aggtgcccta cgtggaccgc aacagctgca agctgtccag cagcttcatc    1200
atcacccaga catgttctg tgccggctac gacaccaagc aggaggatgc ctgccagggg    1260
gacagcgggg gcccgcacgt cacccgcttc aaggacacct acttcgtgac aggcatcgtc    1320
agctggggag agggctgtgc ccgtaagggg aagtacggga tctacaccaa ggtcaccgcc    1380
ttcctcaagt ggatcgacag gtccatgaaa accaggggct gcccaaggc caagagccat    1440
gccccggagg tcataacgtc ctctccattg aaa                                 1473
```

<210> SEQ ID NO 7
<211> LENGTH: 1509
<212> TYPE: DNA
<213> ORGANISM: Artificial Sequence
<220> FEATURE:
<223> OTHER INFORMATION: of modified human FX - type A

<400> SEQUENCE: 7

```
atggcgcacg tccgaggctt gcagctgcct ggctgcctgg ccctggctgc cctgtgtagc      60
```

| | |
|---|---|
| cttgtgcaca gccagcatgt gttcctggct cctcagcaag cacggtcgct gctccagcgg | 120 |
| gtccggcgag ccaattcctt tcttgaagag atgaagaaag acacctcga aagagagtgc | 180 |
| atggaagaga cctgctcata cgaagaggcc cgcgaggtct ttgaggacag cgacaagacg | 240 |
| aatgaattct ggaataaata caaagatggc gaccagtgtg agaccagtcc ttgccagaac | 300 |
| cagggcaaat gtaaagacgg cctcggggaa tacacctgca cctgtttaga aggattcgaa | 360 |
| ggcaaaaact gtgaattatt cacacggaag ctctgcagcc tggacaacgg ggactgtgac | 420 |
| cagttctgcc acgaggaaca gaactctgtg gtgtgctcct gcgcccgcgg gtacaccctg | 480 |
| gctgacaacg gcaaggcctg cattcccaca gggccctacc cctgtgggaa acagaccctg | 540 |
| gaacgcagga gaggtcagt ggcccaggcc accagcagca gcggggaggc ccctgacagc | 600 |
| atcacatgga agccatatga tgcagccgac ctggacccca ccgagaaccc cttcgacctg | 660 |
| cttgacttca accagacgca gcctgagagg ggcgacaaca acctcacgcg tatcgtggga | 720 |
| ggccaggaat gcaaggacgg ggagtgtccc tggcaggccc tgctcatcaa tgaggaaaac | 780 |
| gagggttct gtggtggaac tattctgagc gagttctaca tcctaacggc agcccactgt | 840 |
| ctctaccaag ccaagagatt caaggtgagg gtaggtgacc ggaacacgga gcaggaggag | 900 |
| ggcggtgagg cggtgcacga ggtggaggtg gtcatcaagc acaccaagtt cgtgcccct | 960 |
| aactactatt acgtccacca gaattttgac cgggtggcct atgacttcga catcgccgtg | 1020 |
| ctccggctca agacccccat caccttccgc atgaacgtgg cgcctgcctg cctccccgag | 1080 |
| cgtgactggg ccgagtccac gctgatgacg cagaagacgg ggattgtgag cggcttcggg | 1140 |
| cgcacccacg agaagggccg gcagtccacc aggctcaaga tgctggaggt gcccctacgtg | 1200 |
| gaccgcaaca gctgcaagct gtccagcagc ttcatcatca cccagaacat gttctgtgcc | 1260 |
| ggctacgaca ccaagcagga ggatgcctgc caggggaca gcgggggccc gcacgtcacc | 1320 |
| cgcttcaagg acacctactt cgtgacaggc atcgtcagct ggggagaggg ctgtgcccgt | 1380 |
| aagggggaagt acgggatcta caccaaggtc accgccttcc tcaagtggat cgacaggtcc | 1440 |
| atgaaaacca ggggcttgcc caaggccaag agccatgccc cggaggtcat aacgtcctct | 1500 |
| ccattgaaa | 1509 |

<210> SEQ ID NO 8
<211> LENGTH: 1512
<212> TYPE: DNA
<213> ORGANISM: Artificial Sequence
<220> FEATURE:
<223> OTHER INFORMATION: of modified human FX - type B

<400> SEQUENCE: 8

| | |
|---|---|
| atggcgcacg tccgaggctt gcagctgcct ggctgcctgg ccctggctgc cctgtgtagc | 60 |
| cttgtgcaca gccagcatgt gttcctggct cctcagcaag cacggtcgct gctccagcgg | 120 |
| gtccggcgag ccaattcctt tcttgaagag atgaagaaag acacctcga aagagagtgc | 180 |
| atggaagaga cctgctcata cgaagaggcc cgcgaggtct ttgaggacag cgacaagacg | 240 |
| aatgaattct ggaataaata caaagatggc gaccagtgtg agaccagtcc ttgccagaac | 300 |
| cagggcaaat gtaaagacgg cctcggggaa tacacctgca cctgtttaga aggattcgaa | 360 |
| ggcaaaaact gtgaattatt cacacggaag ctctgcagcc tggacaacgg ggactgtgac | 420 |
| cagttctgcc acgaggaaca gaactctgtg gtgtgctcct gcgcccgcgg gtacaccctg | 480 |
| gctgacaacg gcaaggcctg cattcccaca gggccctacc cctgtgggaa acagaccctg | 540 |
| gaacgcagga gaggtcagt ggcccaggcc accagcagca gcggggaggc ccctgacagc | 600 |

```
atcacatgga agccatatga tgcagccgac ctggacccca ccgagaaccc cttcgacctg    660
cttgacttca accagacgca gcctgagagg ggcgacaaca acctcacgcg tatcgtggga    720
ggccaggaat gcaaggacgg ggagtgtccc tggcaggccc tgctcatcaa tgaggaaaac    780
gagggtttct gtggtggaac tattctgagc gagttctaca tcctaacggc agcccactgt    840
ctctaccaag ccaagagatt caaggtgagg gtaggtgacc ggaacacgga gcaggaggag    900
ggcggtgagc cggtgcacga ggtggaggtg gtcatcaagc acaagaaatt cgtgcccct     960 aagaaaagcc aggagttcta cgaaaagttt gacctggtct cctatgactt cgacatcgcc   1020
gtgctccggc tcaagacccc catcaccttc cgcatgaacg tggcgcctgc ctgcctcccc   1080
gagcgtgact gggccgagtc cacgctgatg acgcagaaga cggggattgt gagcggcttc   1140
gggcgcaccc acgagaaggg ccggcagtcc accaggctca agatgctgga ggtgcctac    1200 gtggaccgca acagctgcaa gctgtccagc agcttcatca tcacccagaa catgttctgt   1260
gccggctacg acaccaagca ggaggatgcc tgccagggg  acagcgggg  cccgcacgtc   1320 acccgcttca aggacaccta cttcgtgaca ggcatcgtca gctggggaga gggctgtgcc   1380
cgtaagggga gtacgggat ctacaccaag gtcaccgcct tcctcaagtg gatcgacagg    1440
tccatgaaaa ccaggggctt gcccaaggcc aagagccatg ccccggaggt cataacgtcc   1500
tctccattga aa                                                      1512
```

<210> SEQ ID NO 9
<211> LENGTH: 21
<212> TYPE: PRT
<213> ORGANISM: Artificial Sequence
<220> FEATURE:
<223> OTHER INFORMATION: chimeric FX type A

<400> SEQUENCE: 9

Lys Lys Phe Val Pro P

<210> SEQ ID NO 12
<211> LENGTH: 6
<212> TYPE: PRT
<213> ORGANISM: Homo sapiens

<400> SEQUENCE: 12

His Asn Arg Phe Thr Lys
1               5

<210> SEQ ID NO 13
<211> LENGTH: 6
<212> TYPE: PRT
<213> ORGANISM: Homo sapiens

<400> SEQUENCE: 13

Glu Thr Tyr Asp Phe Asp
1               5

<210> SEQ ID NO 14
<211> LENGTH: 6
<212> TYPE: PRT
<213> ORGANISM: Mus musculus

<400> SEQUENCE: 14

His Asn Lys Phe Gln Arg
1               5

<210> SEQ ID NO 15
<211> LENGTH: 6
<212> TYPE: PRT
<213> ORGANISM: Mus musculus

<400> SEQUENCE: 15

Asp Thr Tyr Asp Tyr Asp
1               5

<210> SEQ ID NO 16
<211> LENGTH: 6
<212> TYPE: PRT
<213> ORGANISM: Gallus gallus

<400> SEQUENCE: 16

His Ser Lys Tyr Ile Ala
1               5

<210> SEQ ID NO 17
<211> LENGTH: 6
<212> TYPE: PRT
<213> ORGANISM: Gallus gallus

<400> SEQUENCE: 17

Glu Thr Tyr Asp Tyr Asp
1               5

<210> SEQ ID NO 18
<211> LENGTH: 6
<212> TYPE: PRT
<213> ORGANISM: Anolis carolinensis

<400> SEQUENCE: 18

His Gln Lys Phe Val Leu
1               5

```
<210> SEQ ID NO 19
<211> LENGTH: 6
<212> TYPE: PRT
<213> ORGANISM: Anolis carolinensis

<400> SEQUENCE: 19

Ala Thr Tyr Asp Tyr Asp
1               5

<210> SEQ ID NO 20
<211> LENGTH: 6
<212> TYPE: PRT
<213> ORGANISM: Silurana tropicalis

<400> SEQUENCE: 20

His Pro Arg Phe Val Lys
1               5

<210> SEQ ID NO 21
<211> LENGTH: 6
<212> TYPE: PRT
<213> ORGANISM: Silurana tropicalis

<400> SEQUENCE: 21

Ser Thr Tyr Asp Tyr Asp
1               5

<210> SEQ ID NO 22
<211> LENGTH: 6
<212> TYPE: PRT
<213> ORGANISM: Danio rerio

<400> SEQUENCE: 22

His Lys Asn Tyr Gln Pro
1               5

<210> SEQ ID NO 23
<211> LENGTH: 6
<212> TYPE: PRT
<213> ORGANISM: Danio rerio

<400> SEQUENCE: 23

Asp Thr Tyr His Asn Asp
1               5

<210> SEQ ID NO 24
<211> LENGTH: 6
<212> TYPE: PRT
<213> ORGANISM: Takifugu rubripes

<400> SEQUENCE: 24

His Asn Arg Phe Thr Lys
1               5

<210> SEQ ID NO 25
<211> LENGTH: 6
<212> TYPE: PRT
<213> ORGANISM: Takifugu rubripes

<400> SEQUENCE: 25

Asn Thr Tyr His Asn Asp
1               5

<210> SEQ ID NO 26
<211> LENGTH: 6
```

<212> TYPE: PRT
<213> ORGANISM: Pseudonaja textilis

<400> SEQUENCE: 26

His Gln Lys Phe Val Pro
1               5

<210> SEQ ID NO 27
<211> LENGTH: 25
<212> TYPE: PRT
<213> ORGANISM: Pseudonaja textilis

<400> SEQUENCE: 27

His Lys Lys Phe Val Pro Pro Lys Lys Ser Gln Glu Phe Tyr Glu Lys
1               5                   10                  15

Phe Asp Leu Val Ser Tyr Asp Tyr Asp
            20                  25

<210> SEQ ID NO 28
<211> LENGTH: 24
<212> TYPE: PRT
<213> ORGANISM: Notechis scutatus

<400> SEQUENCE: 28

His Thr Lys Phe Val Pro Pro Asn Tyr Tyr Tyr Val His Gln Asn Phe
1               5                   10                  15

Asp Arg Val Ala Tyr Asp Tyr Asp
            20

<210> SEQ ID NO 29
<211> LENGTH: 481
<212> TYPE: PRT
<213> ORGANISM: Mus musculus

<400> SEQUENCE: 29

Met Gly Ser Pro Val Gln Leu Ser Leu Leu Cys Val Val Leu Ala Ser
1               5                   10                  15

Leu Leu Leu Pro Gly Lys Gly Val Phe Ile Asn Arg Glu Arg Ala Asn
            20                  25                  30

Asn Val Leu Ala Arg Thr Arg Arg Ala Asn Ser Phe Phe Glu Glu Phe
        35                  40                  45

Lys Lys Gly Asn Leu Glu Arg Glu Cys Met Glu Glu Ile Cys Ser Tyr
    50                  55                  60

Glu Glu Val Arg Glu Ile Phe Glu Asp Glu Lys Thr Lys Glu Tyr
65                  70                  75                  80

Trp Thr Lys Tyr Lys Asp Gly Asp Gln Cys Glu Ser Ser Pro Cys Gln
                85                  90                  95

Asn Gln Gly Ala Cys Arg Asp Gly Ile Gly Gly Tyr Thr Cys Thr Cys
            100                 105                 110

Ser Glu Gly Phe Glu Gly Lys Asn Cys Glu Leu Phe Val Arg Lys Leu
        115                 120                 125

Cys Arg Leu Asp Asn Gly Asp Cys Asp Gln Phe Cys Arg Glu Glu Gln
    130                 135                 140

Asn Ser Val Val Cys Ser Cys Ala Ser Gly Tyr Phe Leu Gly Asn Asp
145                 150                 155                 160

Gly Lys Ser Cys Ile Ser Thr Ala Pro Phe Pro Cys Gly Lys Ile Thr
                165                 170                 175

Thr Gly Arg Arg Lys Arg Ser Val Ala Leu Asn Thr Ser Asp Ser Glu
            180                 185                 190

```
Leu Asp Leu Glu Asp Ala Leu Leu Asp Glu Asp Phe Leu Ser Pro Thr
            195                 200                 205
Glu Asn Pro Ile Glu Leu Leu Asn Leu Asn Glu Thr Gln Pro Glu Arg
        210                 215                 220
Ser Ser Asp Asp Leu Val Arg Ile Val Gly Gly Arg Glu Cys Lys Asp
225                 230                 235                 240
Gly Glu Cys Pro Trp Gln Ala Leu Leu Ile Asn Glu Asp Asn Glu Gly
                245                 250                 255
Phe Cys Gly Gly Thr Ile Leu Asn Glu Phe Tyr Ile Leu Thr Ala Ala
            260                 265                 270
His Cys Leu His Gln Ala Arg Arg Phe Lys Val Arg Val Gly Asp Arg
        275                 280                 285
Asn Thr Glu Lys Glu Glu Gly Asn Glu Met Val His Glu Val Asp Val
    290                 295                 300
Val Ile Lys His Asn Lys Phe Gln Arg Asp Thr Tyr Asp Tyr Asp Ile
305                 310                 315                 320
Ala Val Leu Arg Leu Lys Thr Pro Ile Thr Phe Arg Met Asn Val Ala
                325                 330                 335
Pro Ala Cys Leu Pro Gln Lys Asp Trp Ala Glu Ser Thr Leu Met Thr
            340                 345                 350
Gln Lys Thr Gly Ile Val Ser Gly Phe Gly Arg Thr His Glu Lys Gly
        355                 360                 365
Arg Gln Ser Asn Ile Leu Lys Met Leu Glu Val Pro Tyr Val Asp Arg
    370                 375                 380
Asn Thr Cys Lys Leu Ser Thr Ser Phe Ser Ile Thr Gln Asn Met Phe
385                 390                 395                 400
Cys Ala Gly Tyr Glu Ala Lys Leu Glu Asp Ala Cys Gln Gly Asp Ser
                405                 410                 415
Gly Gly Pro His Val Thr Arg Phe Lys Asn Thr Tyr Tyr Val Thr Gly
            420                 425                 430
Ile Val Ser Trp Gly Glu Gly Cys Ala Arg Lys Gly Lys Tyr Gly Ile
        435                 440                 445
Tyr Thr Lys Val Thr Thr Phe Leu Lys Trp Ile Asp Arg Ser Met Lys
    450                 455                 460
Ala Arg Val Gly Pro Thr Ala Glu Thr Pro Arg Thr Ala Gly Pro Pro
465                 470                 475                 480
Asn

<210> SEQ ID NO 30
<211> LENGTH: 464
<212> TYPE: PRT
<213> ORGANISM: Silurana tropicalis

<400> SEQUENCE: 30

Met Ala Gly Gln Thr Cys Leu Ile Ile Leu Ile Ala Leu Pro Ala Val
1               5                   10                  15
Leu Leu Gln Gln Ser Pro Asn Val Phe Leu Lys His Glu Asn Ala His
            20                  25                  30
Asn Ile Leu Arg Ala Lys Arg Ala Asn Ser Ala Phe Glu Glu Phe Lys
        35                  40                  45
Lys Gly Asn Leu Glu Arg Glu Cys Tyr Glu Glu Arg Cys Ser Leu Glu
    50                  55                  60
Glu Ala Arg Glu Val Phe Glu Asn Glu Glu Gln Thr Arg Glu Phe Trp
65                  70                  75                  80
```

Ser Lys Tyr Phe Asp Gly Asp Gln Cys Gln Ser Asn Pro Cys Gln Tyr
                85                  90                  95

Gly Gly Ser Cys Asn Asp Gly Ile Asn Glu Tyr Thr Cys Leu Cys Asn
            100                 105                 110

Ala Gly Phe Glu Gly Lys Asn Cys Glu Thr Val Lys Leu Gln Leu Cys
        115                 120                 125

Ser Leu Asn Asn Gly Glu Cys Asp Gln Tyr Cys Lys Ala Val Asp Arg
    130                 135                 140

Asp Val Val Cys Ser Cys Thr Asn Gly Tyr Ile Leu Gly Glu Asn Gly
145                 150                 155                 160

Lys Ser Cys Leu Pro Thr Glu Lys Tyr Ser Cys Gly Arg Arg His Met
                165                 170                 175

Lys Arg Glu Arg Glu Thr Lys Leu His Glu Asn Asp Lys Lys Asn
            180                 185                 190

His Thr Asp Ser Gln Asn Glu Val Lys Met Asn Gln Thr Gly Thr Leu
        195                 200                 205

Pro Glu Arg Asn Val Thr Gly Ile Asn Ile Leu Asn Pro Asn Asp Pro
    210                 215                 220

Asn Val Arg Ile Val Gly Gly Arg Glu Cys Ser Gln Gly Glu Cys Pro
225                 230                 235                 240

Trp Gln Ala Leu Leu Val Ser Asp Glu Asp Glu Gly Phe Cys Gly Gly
                245                 250                 255

Thr Ile Leu Ser Arg Glu Phe Ile Leu Thr Ala Ala His Cys Met Asn
            260                 265                 270

Gln Thr Lys Tyr Phe Lys Val Val Gly Glu Leu Asn Thr Lys Ile
        275                 280                 285

Ser Glu Gly Thr Glu Ser Ile His Lys Val Glu Lys Ile Ile Met His
    290                 295                 300

Pro Arg Phe Val Lys Ser Thr Tyr Asp Tyr Asp Ile Ala Val Ile Lys
305                 310                 315                 320

Leu Lys Glu Ala Ile Asn Phe Thr Glu Asn Ile Ile Pro Ala Cys Ile
                325                 330                 335

Pro Asp Pro Glu Phe Ala Asp Gln Val Leu Met Asn Glu Pro Asp Ala
            340                 345                 350

Met Val Ser Gly Phe Gly Arg Ile His Glu Arg Gly Arg Gln Ala Ser
        355                 360                 365

Thr Leu Gln Met Leu Gln Val Pro Tyr Ile Lys Arg His Ser Cys Lys
    370                 375                 380

Glu Ser Ser Thr Phe Ala Ile Thr Glu Asn Met Phe Cys Ala Gly Phe
385                 390                 395                 400

Asp Thr Glu Val Lys Asp Ala Cys Gln Gly Asp Ser Gly Gly Pro His
                405                 410                 415

Val Thr Pro Phe Lys Gly Thr Tyr Phe Val Thr Gly Ile Val Ser Trp
            420                 425                 430

Gly Glu Gly Cys Ala Arg Lys Gly Lys Phe Gly Val Tyr Thr Lys Val
        435                 440                 445

Ser Lys Leu His Arg Trp Leu Lys Gly Val Leu Lys Lys Asn Gln Val
    450                 455                 460

<210> SEQ ID NO 31
<211> LENGTH: 474
<212> TYPE: PRT
<213> ORGANISM: Danio rerio -continued

```
<400> SEQUENCE: 31

Met Ser Trp Val Phe Trp Asn Phe Ile Ser Leu Phe Val Thr His Ser
1               5                   10                  15

Val Cys Ala Glu Val Phe Leu Asn Thr Arg Asp Ala Asn Gln Val Leu
            20                  25                  30

Ile Arg Gln Arg Arg Ala Asn Ser Leu Phe Glu Met Glu Lys Gly
        35                  40                  45

Asn Met Glu Arg Glu Cys Ile Glu Glu Arg Cys Asn Tyr Glu Glu Ala
    50                  55                  60

Arg Glu Ile Phe Glu Asp Val Lys Lys Thr Asp Glu Phe Trp His Lys
65                  70                  75                  80

Tyr Val Asp Gly Lys Asn Ala Cys Leu Ser His Pro Cys Val Asn Gly
                85                  90                  95

Gly Gln Cys Lys Asp Ala Ile Gly Pro Tyr Thr Cys Phe Cys Gln Gln
            100                 105                 110

Gly Phe Lys Gly Tyr Asn Cys Glu Ile Val Ile Pro Glu Leu Cys Glu
        115                 120                 125

Asn Glu Asn Gly Gly Cys Asp His Phe Cys Glu Val Met Glu Lys Asn
    130                 135                 140

Val Val Cys Ser Cys Ala Asn Gly Tyr Glu Leu Ala Pro Asn Gly Lys
145                 150                 155                 160

Ser Cys Gln Ser Gln Asp Pro Phe Lys Cys Gly Val Ile Tyr Pro Lys
                165                 170                 175

Lys Thr Arg Ser Ile Phe Phe His Thr Pro Asn Ile Thr Glu Ser Glu
            180                 185                 190

Asn Glu Glu Glu Thr Glu Leu Glu Ala Thr Ile Glu Pro Val Tyr Asn
        195                 200                 205

His Ser Asn Pro Leu Asn Asn Gln Thr Asp Ser Met Phe Gly Leu His
    210                 215                 220

Glu Leu Glu Ile Ile Gln Glu Glu Pro Ile Leu Pro Val Val Ser Thr
225                 230                 235                 240

Ala Gly Asp Gly Arg Ile Val Asn Gly Val Glu Cys Pro Pro Gly Asp
                245                 250                 255

Cys Pro Trp Gln Ala Leu Leu Ile Asn Glu Asn Asn Met Gly Phe Cys
            260                 265                 270

Gly Gly Thr Ile Leu Thr Glu His Phe Ile Leu Ser Ala Ala His Cys
        275                 280                 285

Met Asn Glu Ser Leu Ser Ile Arg Val Val Gly Glu Tyr Asp Thr
    290                 295                 300

Leu Val Pro Glu Gly Arg Glu Ala Thr His Asp Val Asp Glu Ile Leu
305                 310                 315                 320

Ile His Lys Asn Tyr Gln Pro Asp Thr Tyr His Asn Asp Ile Ala Leu
                325                 330                 335

Ile Lys Leu Ser Lys Pro Ile Lys Phe Thr Lys Tyr Ile Ile Pro Ala
            340                 345                 350

Cys Leu Pro Glu Met Lys Phe Ala Glu Arg Val Leu Met Gln Gln Asp
        355                 360                 365

Asp Gly Leu Val Ser Gly Phe Gly Arg Val Arg Glu Gly Gly Leu Ser
    370                 375                 380

Ser Thr Ile Leu Gln Lys Leu Thr Val Pro Tyr Val Asn Arg Ala Lys
385                 390                 395                 400

Cys Ile Glu Ser Ser Asn Phe Lys Ile Ser Gly Arg Met Phe Cys Ala
                405                 410                 415
```

Gly Tyr Asp Gln Glu Glu Lys Asp Ala Cys Gln Gly Asp Ser Gly Gly
            420                 425                 430

Pro His Val Thr Arg Phe Lys Asn Thr Trp Phe Ile Thr Gly Val Val
            435                 440                 445

Lys Leu Gly Arg Arg Val Arg Ala Gln Gly Glu Ile Arg Arg Leu His
            450                 455                 460

Thr Gly Leu Gln Ile His His Val Asp Gln
465                 470

<210> SEQ ID NO 32
<211> LENGTH: 475
<212> TYPE: PRT
<213> ORGANISM: Takifugu rubripes

<400> SEQUENCE: 32

Met Phe Arg Leu Phe Phe Ile Ala Phe Leu Asp Lys Thr Gly Ala Ser
1               5                   10                  15

Gln Leu Leu Ser Arg Gln Arg Ala Asn Ser Leu Phe Glu Glu Val
            20                  25                  30

Lys Gln Gly Asn Met Glu Arg Glu Cys Asn Glu Glu His Cys Ser Lys
            35                  40                  45

Glu Glu Ala Arg Glu Ile Phe Glu Asp Asp Gln Thr Asn Glu Phe
            50                  55                  60

Trp Ala Ile Tyr Tyr Asp Gly Asp Ala Cys Lys Ser Thr Pro Cys Val
65                  70                  75                  80

Asn Lys Gly Arg Cys Lys Asp Gly Ile Gly Ser Tyr Thr Cys Phe Cys
                85                  90                  95

Leu Ser Gly Tyr Gln Gly Phe Asn Cys Glu Ile Val Ile Pro Gln Leu
            100                 105                 110

Cys Glu Asn Glu Asn Gly Gly Cys Glu His Phe Cys Lys Val Val Arg
            115                 120                 125

Gly Asn Val Arg Cys Ser Cys Ala Asp Gly Tyr Glu Leu Gly Pro Asp
            130                 135                 140

Asp Lys Ser Cys Gln Ser Asn Glu Thr Phe Arg Cys Gly Gly Ile Ile
145                 150                 155                 160

Thr Glu Asn Val Arg Thr Ile Leu Arg Tyr Arg Pro Asn Thr Asn Thr
                165                 170                 175

Asn Gly Thr Lys Ser Asp Asn Ser Ser Thr Asn Ser Thr Glu Gln
            180                 185                 190

Glu Asp Glu Phe Ser Ser Gly Thr Ser Gln Arg Lys Ala His Ala
            195                 200                 205

Ala Ser Asp His Glu Met Ser Thr Met Thr Arg Ile Val Asn Gly Glu
            210                 215                 220

Asp Cys Pro Pro Gly Glu Cys Pro Trp Gln Ala Val Leu Leu Asn Glu
225                 230                 235                 240

Glu His His Trp Phe Cys Gly Gly Thr Ile Leu Asn Pro Tyr Ile Ile
                245                 250                 255

Leu Thr Ala Ala His Cys Met Asn Glu Thr Arg Tyr Phe Tyr Ile Arg
            260                 265                 270

Leu Gly Glu Ser Asp Met Leu Glu Asn Glu Gly Thr Glu Ala Met Tyr
            275                 280                 285

Glu Val Glu Thr Ile Leu Ala His Tyr Asn Tyr Lys Pro Asn Thr Tyr
            290                 295                 300

His Asn Asp Ile Ala Leu Ile Lys Leu Thr Lys Pro Ile Lys Tyr Ser

```
                305                 310                 315                 320
Arg Phe Ile Leu Pro Ala Cys Ile Pro Glu Gln Glu Phe Ala Glu Ser
                    325                 330                 335

Val Leu Met Gln Gln Ser Asp Gly Met Ile Ser Gly Phe Gly Arg Leu
                    340                 345                 350

Gly Gly Asn Arg Gln Thr Ser Pro Ile Leu Lys Arg Leu Thr Ile Pro
                    355                 360                 365

Tyr Val Glu Arg Arg Thr Cys Met Glu Ser Thr Ser Leu Arg Ile Ser
                370                 375                 380

Ala Arg Met Phe Cys Ala Gly Tyr Asp Glu Ile Ala Lys Asp Ala Cys
385                 390                 395                 400

Gln Gly Asp Ser Gly Gly Pro His Val Thr Arg Tyr Arg Ser Thr Tyr
                    405                 410                 415

Phe Ile Thr Gly Ile Val Ser Trp Gly Glu Gly Cys Ala Gln Lys Gly
                    420                 425                 430

Lys Tyr Gly Val Tyr Thr Gln Val Ser Lys Tyr Ile Arg Trp Ile Arg
                    435                 440                 445

Asp Gly Ile Asn Thr Leu Ile Pro Lys Gly Gln Ser Thr Arg Leu Lys
                    450                 455                 460

Arg His Tyr Gly Pro Ile Arg Arg Ile Val Gly
465                 470                 475

<210> SEQ ID NO 33
<211> LENGTH: 483
<212> TYPE: PRT
<213> ORGANISM: Pseudonaja textilis

<400> SEQUENCE: 33

Met Ala Pro Gln Leu Leu Cys Leu Ile Leu Thr Phe Leu Trp Ser
1                   5                   10                  15

Leu Pro Glu Ala Glu Ser Asn Val Phe Leu Lys Ser Lys Val Ala Asn
                    20                  25                  30

Arg Phe Leu Gln Arg Thr Lys Arg Ala Asn Ser Leu Phe Glu Glu Phe
                    35                  40                  45

Lys Ser Gly Asn Ile Glu Arg Glu Cys Ile Glu Glu Arg Cys Ser Lys
                50                  55                  60

Glu Glu Ala Arg Glu Ala Phe Glu Asp Glu Lys Thr Glu Thr Phe
65                  70                  75                  80

Trp Asn Val Tyr Val Asp Gly Asp Gln Cys Ser Ser Asn Pro Cys His
                    85                  90                  95

Tyr Gly Gly Thr Cys Lys Asp Gly Ile Gly Ser Tyr Thr Cys Thr Cys
                    100                 105                 110

Leu Ser Gly Tyr Glu Gly Lys Asn Cys Glu Tyr Val Leu Tyr Lys Ser
                    115                 120                 125

Cys Arg Val Asp Asn Gly Asp Cys Trp His Phe Cys Lys Pro Val Gln
                130                 135                 140

Asn Gly Ile Gln Cys Ser Cys Ala Glu Ser Tyr Leu Leu Gly Glu Asp
145                 150                 155                 160

Gly His Ser Cys Val Ala Gly Gly Asp Phe Ser Cys Gly Arg Asn Ile
                    165                 170                 175

Lys Thr Arg Asn Lys Arg Glu Ala Asn Leu Pro Asp Phe Gln Thr Asp
                    180                 185                 190

Phe Ser Asp Asp Tyr Asp Glu Ile Asp Glu Asn Asn Phe Val Glu Thr
                    195                 200                 205
```

```
Pro Thr Asn Phe Ser Gly Leu Val Leu Thr Val Gln Ser Gln Asn Ala
    210                 215                 220

Thr Leu Leu Lys Lys Ser Asp Asn Pro Ser Pro Asp Ile Arg Val Val
225                 230                 235                 240

Asn Gly Thr Asp Cys Lys Leu Gly Glu Cys Pro Trp Gln Ala Leu Leu
                245                 250                 255

Leu Asn Asp Glu Gly Asp Gly Phe Cys Gly Gly Thr Ile Leu Ser Pro
                260                 265                 270

Ile Tyr Val Leu Thr Ala Ala His Cys Ile Asn Gln Thr Lys Tyr Ile
                275                 280                 285

Thr Val Val Val Gly Glu Ile Asp Ile Ser Ser Lys Lys Thr Gly Arg
                290                 295                 300

Leu His Ser Val Asp Lys Ile Tyr Val His Gln Lys Phe Val Pro Ala
305                 310                 315                 320

Thr Tyr Asp Tyr Asp Ile Ala Ile Ile Gln Leu Lys Thr Pro Ile Gln
                    325                 330                 335

Phe Ser Glu Asn Val Val Pro Ala Cys Leu Pro Thr Ala Asp Phe Ala
                340                 345                 350

Asn Gln Val Leu Met Lys Gln Asn Phe Gly Ile Val Ser Gly Phe Gly
                355                 360                 365

Arg Thr Arg Glu Arg Gly Lys Thr Ser Asn Thr Leu Lys Val Val Thr
370                 375                 380

Leu Pro Tyr Val Asp Arg His Thr Cys Met Leu Ser Ser Asn Phe Pro
385                 390                 395                 400

Ile Thr Gln Asn Met Phe Cys Ala Gly Tyr Asp Thr Leu Pro Gln Asp
                    405                 410                 415

Ala Cys Gln Gly Asp Ser Gly Gly Pro His Ile Thr Ala Tyr Arg Asp
                420                 425                 430

Thr His Phe Ile Thr Gly Ile Val Ser Trp Gly Glu Gly Cys Ala Gln
                435                 440                 445

Thr Gly Lys Tyr Gly Val Tyr Thr Lys Val Ser Lys Phe Ile Leu Trp
                450                 455                 460

Ile Lys Arg Ile Ile Arg Gln Lys Gln Pro Ser Thr Glu Ser Ser Thr
465                 470                 475                 480

Gly Arg Leu

<210> SEQ ID NO 34
<211> LENGTH: 463
<212> TYPE: PRT
<213> ORGANISM: Pseudonaja textilis

<400> SEQUENCE: 34

Met Ala Pro Gln Leu Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ala Asn Ser Leu Val Glu Glu Phe
            35                  40                  45

Lys Ser Gly Asn Ile Glu Arg Glu Cys Ile Glu Glu Arg Cys Ser Lys
        50                  55                  60

Glu Glu Ala Arg Glu Ala Phe Glu Asp Asp Lys Thr Glu Thr Phe
65                  70                  75                  80

Trp Asn Val Tyr Val Asp Gly Asp Gln Cys Ser Ser Asn Pro Cys His
                85                  90                  95
```

```
Tyr Arg Gly Ile Cys Lys Asp Gly Ile Gly Ser Tyr Thr Cys Thr Cys
                100                 105                 110

Leu Ser Gly Tyr Glu Gly Lys Asn Cys Glu Arg Val Leu Tyr Lys Ser
            115                 120                 125

Cys Arg Val Asp Asn Gly Asn Cys Trp His Phe Cys Lys His Val Gln
        130                 135                 140

Asn Asp Ile Gln Cys Ser Cys Ala Glu Gly Tyr Leu Leu Gly Glu Asp
145                 150                 155                 160

Gly His Ser Cys Val Ala Gly Gly Asn Phe Ser Cys Gly Arg Asn Ile
                165                 170                 175

Lys Thr Arg Asn Lys Arg Glu Ala Asn Leu Pro Asp Phe Val Gln Ser
            180                 185                 190

Gln Asn Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
210                 215                 220

Ala Ala Leu Val Asp Glu Lys Glu Gly Val Phe Cys Gly Gly Thr Ile
225                 230                 235                 240

Leu Ser Pro Ile Tyr Val Leu Thr Ala Ala His Cys Ile Asn Glu Thr
                245                 250                 255

Glu Thr Ile Ser Val Val Gly Glu Ile Asp Lys Ser Arg Ile Glu
            260                 265                 270

Thr Gly Pro Leu Leu Ser Val Asp Lys Ile Tyr Val His Lys Lys Phe
            275                 280                 285

Val Pro Pro Gln Lys Ala Tyr Lys Phe Asp Leu Ala Ala Tyr Asp Tyr
        290                 295                 300

Asp Ile Ala Ile Ile Gln Met Lys Thr Pro Ile Gln Phe Ser Glu Asn
305                 310                 315                 320

Val Val Pro Ala Cys Leu Pro Thr Ala Asp Phe Ala Asn Gln Val Leu
                325                 330                 335

Met Lys Gln Asp Phe Gly Ile Val Ser Gly Phe Gly Arg Ile Phe Glu
            340                 345                 350

Lys Gly Pro Lys Ser Lys Thr Leu Lys Val Leu Lys Val Pro Tyr Val
        355                 360                 365

Asp Arg His Thr Cys Met Val Ser Ser Glu Pro Ile Thr Pro Asn
370                 375                 380

Met Phe Cys Ala Gly Tyr Asp Thr Leu Pro Arg Asp Ala Cys Gln Gly
385                 390                 395                 400

Asp Ser Gly Gly Pro His Thr Thr Val Tyr Arg Asp Thr His Phe Ile
                405                 410                 415

Thr Gly Ile Val Ser Ser Gly Glu Gly Cys Ala Arg Asn Gly Lys Tyr
            420                 425                 430

Gly Ile Tyr Thr Lys Leu Ser Lys Phe Ile Pro Trp Ile Lys Arg Ile
        435                 440                 445

Met Arg Gln Lys Leu Pro Ser Thr Glu Ser Ser Thr Gly Arg Leu
450                 455                 460

<210> SEQ ID NO 35
<211> LENGTH: 449
<212> TYPE: PRT
<213> ORGANISM: Pseudonaja textilis

<400> SEQUENCE: 35

Met Ala Pro Gln Leu Leu Leu Cys Leu Ile Leu Thr Phe Leu Trp Ser
1               5                   10                  15
```

```
Leu Pro Glu Ala Glu Ser Asn Val Phe Leu Lys Ser Lys Val Ala Asn
            20                  25                  30
Arg Phe Leu Gln Arg Thr Lys Arg Ala Asn Ser Leu Val Glu Glu Phe
        35                  40                  45
Lys Ser Gly Asn Ile Glu Arg Glu Cys Ile Glu Glu Arg Cys Ser Lys
50                  55                  60
Glu Glu Ala Arg Glu Ala Phe Glu Asp Asp Glu Lys Thr Glu Thr Phe
65                  70                  75                  80
Trp Asn Val Tyr Val Asp Gly Asp Gln Cys Ser Ser Asn Pro Cys His
                85                  90                  95
Tyr Arg Gly Ile Cys Lys Asp Gly Ile Gly Ser Tyr Thr Cys Thr Cys
                100                 105                 110
Leu Ser Gly Tyr Glu Gly Lys Asn Cys Glu Arg Val Leu Tyr Lys Ser
            115                 120                 125
Cys Arg Val Asp Asn Gly Asn Cys Trp His Phe Cys Lys Ser Val Gln
130                 135                 140
Asn Asp Ile Gln Cys Ser Cys Ala Glu Gly Tyr Leu Leu Gly Glu Asp
145                 150                 155                 160
Gly His Ser Cys Val Ala Gly Gly Asn Phe Ser Cys Gly Arg Asn Ile
                165                 170                 175
Lys Thr Arg Asn Lys Arg Glu Ala Ser Leu Pro Asp Phe Val Gln Ser
            180                 185                 190
Gln Asn Ala Pro Leu Leu Lys Ile Ser Asp Asn Pro Ser Pro Asp Ile
        195                 200                 205
Arg Ile Val Asn Gly Met Asp Cys Lys Leu Gly Glu Cys Pro Trp Gln
210                 215                 220
Ala Ala Leu Val Asp Asp Lys Lys Gly Val Phe Cys Gly Gly Thr Ile
225                 230                 235                 240
Leu Ser Pro Ile Tyr Val Leu Thr Ala Ala His Cys Ile Asn Glu Thr
                245                 250                 255
Glu Thr Ile Ser Val Val Gly Glu Ile Asp Arg Ser Arg Ala Glu
            260                 265                 270
Thr Gly Pro Leu Leu Ser Val Asp Lys Val Tyr Val His Lys Lys Phe
            275                 280                 285
Val Pro Pro Lys Lys Ser Gln Glu Phe Tyr Glu Lys Phe Asp Leu Val
290                 295                 300
Ser Tyr Asp Tyr Asp Ile Ala Ile Ile Gln Met Lys Thr Pro Ile Gln
305                 310                 315                 320
Phe Ser Glu Asn Val Val Pro Ala Cys Leu Pro Thr Ala Asp Phe Ala
                325                 330                 335
Asn Gln Val Leu Met Lys Gln Asp Phe Gly Ile Val Ser Gly Phe Gly
            340                 345                 350
Gly Ile Phe Glu Arg Gly Pro Asn Ser Lys Thr Leu Lys Val Leu Lys
        355                 360                 365
Val Pro Tyr Val Asp Arg His Thr Cys Met Leu Ser Ser Asn Phe Pro
370                 375                 380
Ile Thr Pro Thr Met Phe Cys Ala Gly Tyr Asp Thr Leu Pro Gln Asp
385                 390                 395                 400
Ala Cys Gln Gly Asp Ser Gly Gly Pro His Ile Thr Ala Tyr Arg Asp
                405                 410                 415
Thr His Phe Ile Thr Gly Ile Val Ser Trp Gly Glu Gly Cys Ala Arg
            420                 425                 430
```

```
Lys Gly Arg Tyr Gly Ile Tyr Thr Lys Leu Ser Lys Phe Ile Pro Trp
            435                 440                 445
Ile
```

<210> SEQ ID NO 36
<211> LENGTH: 455
<212> TYPE: PRT
<213> ORGANISM: Notechis scutatus

<400> SEQUENCE: 36

```
Met Ala Pro Gln Leu Leu Cys Leu Ile Leu Thr Phe Leu Trp Ser
1               5                   10                  15

Leu Pro Glu Ala Glu Ser Asn Val Phe Leu Lys Ser Lys Val Ala Asn
                20                  25                  30

Arg Phe Leu Gln Arg Thr Lys Arg Ser Asn Ser Leu Phe Glu Glu Ile
            35                  40                  45

Arg Pro Gly Asn Ile Glu Arg Glu Cys Ile Glu Glu Lys Cys Ser Lys
        50                  55                  60

Glu Glu Ala Arg Glu Val Phe Glu Asp Asn Glu Lys Thr Glu Thr Phe
65                  70                  75                  80

Trp Asn Val Tyr Val Asp Gly Asp Gln Cys Ser Ser Asn Pro Cys His
                85                  90                  95

Tyr Arg Gly Thr Cys Lys Asp Gly Ile Gly Ser Tyr Thr Cys Thr Cys
            100                 105                 110

Leu Pro Asn Tyr Glu Gly Lys Asn Cys Glu Lys Val Leu Tyr Gln Ser
        115                 120                 125

Cys Arg Val Asp Asn Gly Asn Cys Trp His Phe Cys Lys Arg Val Gln
130                 135                 140

Ser Glu Thr Gln Cys Ser Cys Ala Glu Ser Tyr Arg Leu Gly Val Asp
145                 150                 155                 160

Gly His Ser Cys Val Ala Glu Gly Asp Phe Ser Cys Gly Arg Asn Ile
                165                 170                 175

Lys Ala Arg Asn Lys Arg Glu Ala Ser Leu Pro Asp Phe Val Gln Ser
            180                 185                 190

Gln Lys Ala Thr Leu Leu Lys Lys Ser Asp Asn Pro Ser Pro Asp Ile
        195                 200                 205

Arg Ile Val Asn Gly Met Asp Cys Lys Leu Gly Glu Cys Pro Trp Gln
210                 215                 220

Ala Val Leu Ile Asn Glu Lys Gly Glu Val Phe Cys Gly Gly Thr Ile
225                 230                 235                 240

Leu Ser Pro Ile His Val Leu Thr Ala Ala His Cys Ile Asn Gln Thr
                245                 250                 255

Lys Ser Val Ser Val Ile Val Gly Glu Ile Asp Ile Ser Arg Lys Glu
            260                 265                 270

Thr Arg Arg Leu Leu Ser Val Asp Lys Ile Tyr Val His Thr Lys Phe
        275                 280                 285

Val Pro Pro Asn Tyr Tyr Val His Gln Asn Phe Asp Arg Val Ala
        290                 295                 300

Tyr Asp Tyr Asp Ile Ala Ile Ile Arg Met Lys Thr Pro Ile Gln Phe
305                 310                 315                 320

Ser Glu Asn Val Val Pro Ala Cys Leu Pro Thr Ala Asp Phe Ala Asn
                325                 330                 335

Glu Val Leu Met Lys Gln Asp Ser Gly Ile Val Ser Gly Phe Gly Arg
            340                 345                 350
```

```
Ile Arg Phe Lys Glu Pro Thr Ser Asn Thr Leu Lys Val Ile Thr Val
            355                 360                 365

Pro Tyr Val Asp Arg His Thr Cys Met Leu Ser Ser Asp Phe Arg Ile
    370                 375                 380

Thr Gln Asn Met Phe Cys Ala Gly Tyr Asp Thr Leu Pro Gln Asp Ala
385                 390                 395                 400

Cys Gln Gly Asp Ser Gly Gly Pro His Ile Thr Ala Tyr Arg Asp Thr
                405                 410                 415

His Phe Ile Thr Gly Ile Ile Ser Trp Gly Glu Gly Cys Ala Arg Lys
            420                 425                 430

Gly Lys Tyr Gly Val Tyr Thr Lys Val Ser Arg Phe Ile Pro Trp Ile
            435                 440                 445

Lys Lys Ile Met Ser Leu Lys
450                 455

<210> SEQ ID NO 37
<211> LENGTH: 8
<212> TYPE: PRT
<213> ORGANISM: Homo sapiens

<400> SEQUENCE: 37

Asn Arg Phe Thr Lys Glu Thr Tyr
1               5
```

What is claimed is:

1. A method of completely or partially reversing an anti-coagulant effect of a direct factor Xa inhibitor in a subject, the method comprising:
administering to the subject an amount of a protein comprising a coagulation factor Xa polypeptide having an alteration in a region of amino acid residues corresponding to the region of amino acid residues between His-311 and Asp-320 of SEQ ID NO: 1, wherein the alteration is an insertion of from 1-20 amino acid residues,
wherein the amount is sufficient to at least partially reverse the anti-coagulant effect of the direct factor Xa inhibitor in the subject.

2. The method according to claim 1, wherein the direct factor Xa inhibitor is selected from the group consisting of rivaroxaban (5-chloro-N-[[(5S)-2-oxo-3-[4-(3-oxo-4-morpholinyl)phenyl]-5-oxazolidinyl]methyl]-2-thiophenecarboxamide), apixaban (1-(4methoxyphenyl)-7-oxo-6-[4-(2-oxopiperidin-1-yl)phenyl]-4,5,6,7-tetrahydro-1H-pyrazolo[3,4-c]pyridine-3-carboxamide), edoxaban (N'-(5-chloropyridin-2-yl)-N-[(1S,2R,4S)-4-(dimethylcarbamoyl)-2-[(5-methyl-6,7-dihydro-4H-[1,3]thiazolo[5,4-c]pyridine-2-carbonyl)amino]cyclohexyl]oxamide; 4-methylbenzenesulfonic acid), and betrixaban (N-(5-chloropyridin-2-yl)-2-[[4-(N,N-dimethylcarbamimidoyl)benzoyl]amino]-5-methoxybenzamide).

3. The method according to claim 1, wherein said insertion is between two amino acid residues corresponding to Lys-316 and Glu-317 of SEQ ID NO: 1.

4. The method according to claim 1, wherein the insertion of from 1-20 amino acid residues is combined with a replacement of between 1-8 amino acid residues in the region of amino acid residues between His-311 and Asp-320 of SEQ ID NO: 1.

* * * * *